US012220163B2

United States Patent
Tse et al.

(10) Patent No.: US 12,220,163 B2
(45) Date of Patent: Feb. 11, 2025

(54) WIRELESSLY POWERED TISSUE ABLATION DEVICE

(71) Applicant: UNIVERSITY OF GEORGIA RESEARCH FOUNDATION, INC., Athens, GA (US)

(72) Inventors: Tsz Ho Tse, Lawrenceville, GA (US); Julian Malik Moore, Smyrna, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 699 days.

(21) Appl. No.: 16/428,170

(22) Filed: May 31, 2019

(65) Prior Publication Data

US 2019/0365465 A1  Dec. 5, 2019

Related U.S. Application Data

(60) Provisional application No. 62/679,192, filed on Jun. 1, 2018.

(51) Int. Cl.
| | |
|---|---|
| *A61B 18/14* | (2006.01) |
| *A61B 17/00* | (2006.01) |
| *A61B 18/00* | (2006.01) |
| *A61B 18/12* | (2006.01) |

(52) U.S. Cl.
CPC ...... *A61B 18/1492* (2013.01); *A61B 18/1206* (2013.01); *A61B 2017/00734* (2013.01); *A61B 2018/00577* (2013.01); *A61B 2018/00767* (2013.01); *A61B 2018/126* (2013.01)

(58) Field of Classification Search
None
See application file for complete search history.

(56) References Cited

U.S. PATENT DOCUMENTS

| | | | | |
|---|---|---|---|---|
| 5,312,401 A | * | 5/1994 | Newton | A61B 18/14 606/42 |
| 2011/0160514 A1 | * | 6/2011 | Long | A61B 18/1477 606/41 |
| 2017/0035402 A1 | * | 2/2017 | Matsui | A61B 18/14 |

(Continued)

FOREIGN PATENT DOCUMENTS

WO    2017/160808    9/2017

OTHER PUBLICATIONS

Annotated Newton Fig 2 (Year: 2022).*

(Continued)

*Primary Examiner* — Linda C Dvorak
*Assistant Examiner* — Nicholas S Borsch
(74) *Attorney, Agent, or Firm* — Meunier Carlin & Curfman LLC

(57) ABSTRACT

Disclosed herein are wirelessly powered tissue ablation devices comprising an alternating magnetic field generator; an ablation probe comprising an ablation tip; a catheter comprising an opening at a tissue insertion end and a lumen extending along a length of the catheter to the catheter opening; and a magnetic field receiving coil configured to be electrically coupled to the ablation probe; wherein at least a portion of the ablation probe is positionable within the lumen of the catheter, and wherein the ablation tip protrudes through the opening of the catheter. Also disclosed are methods of using wirelessly powered tissue ablation devices.

20 Claims, 14 Drawing Sheets

(56) References Cited

U.S. PATENT DOCUMENTS

2017/0065324 A1    3/2017   Attaluri et al.
2018/0206884 A1*   7/2018   Beaupre ............... A61B 18/14

OTHER PUBLICATIONS

Annotated Matsui Fig 2 (Year: 2024).*

Berjano, Enrique J. "Theoretical modeling for radiofrequency ablation: state-of-the-art and challenges for the future." Biomedical engineering online 5.1 (2006): 24.

Blessing, Erwin, et al. "Cardiac ablation and renal denervation systems have distinct purposes and different technical requirements." JACC: Cardiovascular Interventions 6.3 (2013): 314.

Boeti, Mirela Patricia Sîrb, Răzvan Grigorie, and Irinel Popescu. "Laparoscopic radiofrequency ablation of liver tumors." Hepatic Surgery. IntechOpen, 2013.

Brace, "Radiofrequency and microwave ablation of the liver, lung, kidney, and bone: what are the differences?" Current problems in diagnostic radiology, vol. 38, No. 3, pp. 135-143, 2009.

Costanzo A, Dionigi M, Mastri F, Mongiardo M. "Rigorous modeling of mid-range wireless power transfer systems based on Royer oscillators". Proc. 2013 IEEE Wireless Power Transfer (WPT), 2013:69-72: IEEE.

Curley SAJAoSO. 2003. "Radiofrequency ablation of malignant liver tumors". 10:338-47.

Decadt B, Siriwardena AKJTlo. 2004. "Radiofrequency ablation of liver tumours: systematic review". 5:550-60.

Goldberg, G. S. Gazelle, L. Solbiati, W. J. Rittman, and P. R. Mueller, "Radiofrequency tissue ablation: increased lesion diameter with a perfusion electrode," Academic radiology, vol. 3, No. 8, pp. 636-644, 1996.

Goldberg, M. C. Stein, G. S. Gazelle, R. G. Sheiman, J. B. Kruskal, and M. E. Clouse, "Percutaneous radiofrequency tissue ablation: optimization of pulsed-radiofrequency technique to increase coagulation necrosis," Journal of vascular and interventional radiology, vol. 10, No. 7, pp. 907-916, 1999.

Haemmerich D, Staelin T, Tungjitkusolmun S, Lee FT, Mahvi DM, Webster JG. 2001, "Hepatic bipolar radio-frequency ablation between separated multiprong electrodes". IEEE Transactions on Biomedical Engineering 48:1145-52.

Haemmerich D. 2010. "Biophysics of radiofrequency ablation. Critical Reviews™", in Biomedical Engineering 38:1, 16 pages.

Haemmerich D. "Mathematical modeling of impedance controlled radiofrequency tumor ablation and ex-vivo validation". Proc. Engineering in Medicine and Biology Society (EMBC), 2010 Annual International Conference of the IEEE, 2010:1605-8: IEEE.

Haines, "The biophysics of radiofrequency catheter ablation in the heart: the importance of temperature monitoring," Pacing and Clinical Electrophysiology, vol. 16, No. 3, pp. 586-591, 1993.

Jesus, J. Machado, J. B. Cunha, and M. F. Silva, "Fractional order electrical impedance of fruits and vegetables," in Proceedings of the 25th IASTED international conference on Modeling, identification, and control, 2006, pp. 489-494: ACTA Press.

Joo, Young-Chan, Ju-Yeon Park, and Kyung-Hoon Kim. "Comparison of alcohol ablation with repeated thermal radiofrequency ablation in medial branch neurotomy for the treatment of recurrent thoracolumbar facet joint pain." Journal of anesthesia 27.3 (2013): 390-395.

Kovoor, Pramesh, et al. "Effect of Inter-electrode Distance on Bipolar Intramural Radiofrequency Ablation." Pacing and clinical electrophysiology 28.6 (2005): 514-520.

Labonte, "Numerical model for radio-frequency ablation of the endocardium and its experimental validation," IEEE Transactions on Biomedical Engineering, vol. 41, No. 2, pp. 108-115, 1994.

Livraghi, Tito, et al. "Small hepatocellular carcinoma: treatment with radio-frequency ablation versus ethanol injection." Radiology 210.3 (1999): 655-661.

Machi, Junji, et al. "Ultrasound-guided radiofrequency thermal ablation of liver tumors: percutaneous, laparoscopic, and open surgical approaches." Journal of Gastrointestinal Surgery 5.5 (2001): 477-489.

Mastri F, Costanzo A, Dionigi M, Mongiardo M. "Harmonic balance design of wireless resonant-type power transfer links". Proc. 2012 IEEE MTT-S International Microwave Workshop Series on Innovative Wireless Power Transmission: Technologies, Systems, and Applications, 2012:245-8: IEEE.

McGahan, John P., and Gerald D. Dodd III. "Radiofrequency ablation of the liver: current status." American Journal of Roentgenology 176.1 (2001): 3-16.

Mirza, Attiqa N., et al. "Radiofrequency ablation of solid tumors." Cancer journal (Sudbury, Mass.) 7.2 (2001): 95-102.

Morimoto T, Kimura S, Konishi Y, Komaki K, Uyama T, et al. 1993. "A Study of the Electrical Bio-impedance of Tumors". Journal of Investigative Surgery 6:25-32.

Nakada, Stephen Y., et al. "Bipolar radiofrequency ablation of the kidney: comparison with monopolar radiofrequency ablation." Journal of endourology 17.10 (2003): 927-933.

Patel, Nilesh, et al. "A randomized, placebo-controlled study to assess the efficacy of lateral branch neurotomy for chronic sacroiliac joint pain." Pain Medicine 13.3 (2012): 383-398.

Pearson, A. Scott, et al. "Intraoperative radiofrequency ablation or cryoablation for hepatic malignancies." The American journal of surgery 178.6 (1999): 592-598.

Souchon, Rémi, et al. "Visualisation of HIFU lesions using elastography of the human prostate in vivo: preliminary results." Ultrasound in medicine & biology 29.7 (2003): 1007-1015.

Stielau OH, Covic GA. "Design of loosely coupled inductive power transfer systems". Proc. PowerCon 2000. 2000 International Conference on Power System Technology. Proceedings (Cat. No. 00EX409), 2000, 1:85-90: IEEE.

Vogel, Alfred, and Vasan Venugopalan. "Mechanisms of pulsed laser ablation of biological tissues." Chemical reviews 103.2 (2003): 577-644.

* cited by examiner

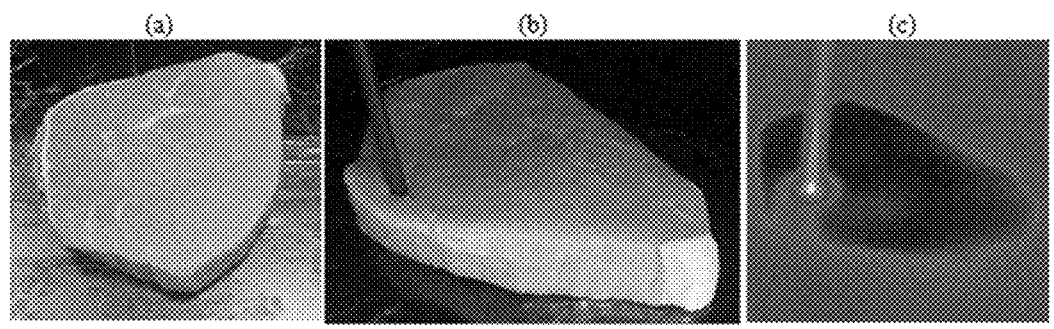
FIGURE 12A-C

WIRELESSLY POWERED TISSUE ABLATION DEVICE

CROSS-REFERENCE TO RELATED APPLICATIONS

This application claims benefit of U.S. Provisional Application No. 62/679,192, filed Jun. 1, 2018, incorporated herein by reference in its entirety.

STATEMENT REGARDING FEDERALLY SPONSORED RESEARCH

This invention was made with government support under Grant No. UL1TR000454 awarded by the National Institutes of Health. The Government has certain rights in the invention.

FIELD

The disclosure generally relates to tissue ablation devices having a wirelessly powered generator and ablation probe, and methods of using wirelessly powered tissue ablation devices.

BACKGROUND

Thermal ablation is a minimally invasive medical procedure in which tissues, most commonly cancerous tumors, are heated to cytotoxic temperatures. Temperatures above 60° C. will cause destruction at the cellular level, leading to cell death. Radiofrequency ablation (RFA) uses electrical current that alternates at radio frequencies between two electrodes (C. L. Brace, *Current Problems in Diagnostic Radiology*, vol. 38, no. 3, pp. 135-143, 2009; D. E. Haines, *Pacing and Clinical Electrophysiology*, vol. 16, no. 3, pp. 586-591, 1993; Goldberg et al. *Academic Radiology*, vol. 3, no. 8, pp. 636-644, 1996).

In monopolar RFA, one electrode is inserted into the body on a catheter and the other electrode is in contact with the skin. In bipolar RFA, both electrodes are inserted into the body and the current flows between them. Bipolar RFA provides a more accurate method to direct the current flow. Both electrodes can be connected to one catheter (S. Labonte, *IEEE Transactions on Biomedical Engineering*, vol. 41, no. 2, pp. 108-115, 1994; E. J. Berjano, *Biomedical engineering online*, vol. 5, no. 1, p. 24, 2006; S. N. Goldberg et al. *Journal of Vascular and Interventional Radiology*, vol. 10, no. 7, pp. 907-916, 1999; I. S. Jesus et al. in *Proceedings of the 25th IASTED International Conference on Modeling, Indentification, and Control*, 2006, pp. 489-494: ACTA Press).

The probe is inserted into the body and contacts the part of tissue the operator wishes to ablate. The tissue introduces a resistance and thus completes a circuit between the two electrodes. When current is introduced to tissue, the ions in the body align in the direction of the current. When that current alternates at high frequencies, the ions agitate, creating heat which causes tissue coagulation, thus resulting in cell death (D. Haemmerich et al. *IEEE Transactions on Biomedical Engineering*, vol. 48, no. 10, pp. 1145-1152, 2001; D. Haemmerich, in *Engineering in Medicine and Biology Society (EMBC)*, 2010 *Annual International Conference of the IEEE*, 2010, pp. 1605-1608: IEEE).

This technique appeals to many patients who cannot have surgery or choose to avoid it because it is highly invasive and can pose great risks. Ablation only requires catheter-sized incisions rather than the larger incisions required in major surgeries. Current ablation techniques use several cords and wires that complicate the procedure. There is also a risk for wires to be cut or shorted when any sharp metal object is present. The devices and methods disclosed herein can declutter and streamline this procedure using electromagnetic induction.

The compositions and methods disclosed herein address these and other needs.

SUMMARY

The disclosed subject matter relates to devices and methods for treating tissue (e.g., ablating tissue) using wireless power transfer.

In one aspect, disclosed herein is a wireless tissue ablation device comprising an alternating magnetic field generator; an ablation probe comprising an ablation tip; a catheter comprising an opening at a tissue insertion end and a lumen extending along a length of the catheter to the catheter opening; and a magnetic field receiving coil configured to be electrically coupled to the ablation probe; wherein at least a portion of the ablation probe is positionable within the lumen of the catheter, and wherein the ablation tip protrudes through the opening of the catheter. In some embodiments, the alternating magnetic field generator comprises a magnetic field transmitting coil, which can be powered by a battery. In some embodiments, the alternating magnetic field generator is comprised within a portable housing, which can comprise an elongated bottom surface configured to contact the subject. The portable housing can also comprise a top surface and an access opening extending from the top surface to the elongated bottom surface, wherein the access opening provides access to the subject upon positioning the portable housing on the subject. In some embodiments, the access opening of the portable housing has a width of five inches or less. In some embodiments, the portion of the ablation probe positionable within the lumen of the catheter comprises a probe outer surface electrical insulator. In some embodiments, the magnetic field transmitting coil and the magnetic field receiving coil are configured to resonate at a frequency from about 200 kHz to about 240 kHz. In some embodiments, the magnetic field receiving coil is positioned on an electrically insulated stop barrier attached to the catheter.

In another aspect, provided herein are methods of ablating a target tissue in a subject, the methods comprising positioning in the subject a catheter comprising an opening at a tissue insertion end and a lumen; contacting the target tissue with an ablation tip of an ablation probe, wherein at least a portion of the ablation probe is positioned within the lumen of the catheter, and wherein the ablation tip protrudes through the opening of the catheter; generating a magnetic field from an alternating magnetic field generator to wirelessly induce a current in a magnetic field receiving coil electrically coupled to the ablation probe; and electrically energizing the ablation tip, thereby ablating the target tissue. In some embodiments, the alternating magnetic field generator comprises a magnetic field transmitting coil and can be comprised within a portable housing. In some embodiments, the portable housing can be positioned on the subject (e.g., adjacent to a catheter insertion point). In some embodiments, the magnetic field receiving coil is coupled to the catheter such that positioning the catheter in the subject also positions the magnetic field receiving coil within a close distance (e.g., 12 cm or less) of the alternating magnetic field generator. In some embodiments, the magnetic field transmitting coil and the magnetic field receiving coil each oscillate within a range of frequencies from 200 kHz to 240 kHz. In some embodiments, the oscillation frequency of the magnetic field receiving coil is within 5 kHz of the oscillation frequency of the magnetic field transmitting coil. In some embodiments, the method further comprises coupling a resonance converter to the magnetic receiving coil, wherein the resonance converter adjusts the current to maintain resonance coupling between the magnetic field receiving coil and the magnetic field transmitting coil. In some embodiments, the alternating magnetic field generator has a power output of at least 40 W, and the ablation probe has a power output of at least 15 W. In some embodiments, the target tissue, which can comprise a tumor, is ablated for 60 seconds or less. In some embodiments, the method is performed outside of an operating room. In some embodiments, the method ablates a zone of target tissue having a width of 30 mm or less and/or increases temperature of the target tissue to at least 60° C.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are exemplary and explanatory only and are not restrictive of the disclosure.

BRIEF DESCRIPTION OF THE DRAWINGS

The accompanying drawings, which are incorporated in and constitute a part of this specification, illustrate certain examples of the present disclosure and together with the description, serve to explain, without limitation, the principles of the disclosure. Like numbers represent the same element(s) throughout the figures.

FIG. 1(A-B) is a schematic showing circuit diagrams.

FIG. 3(A-B) are images showing a wireless ablation catheter.

FIG. 12A-C shows setup of the bovine liver experiment (A) ex vivo bovine tissue before ablation, (B) tissue during ablation (C) thermal image during ablation.

DETAILED DESCRIPTION

Figure 1A:
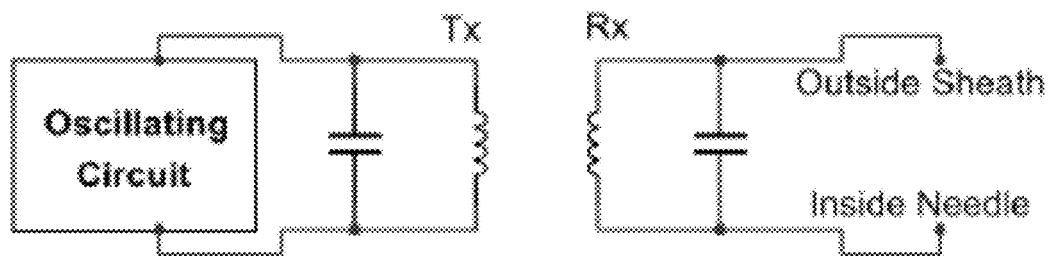
FIG. 1A shows the general layout of the circuitry.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this invention belongs. The following definitions are provided for the full understanding of terms used in this specification.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular coil is disclosed and discussed and a number of modifications that can be made to the coil are discussed, specifically contemplated is each and every combination and permutation of the coil and the modifications that are possible unless specifically indicated to the contrary. Thus, if a class of coils A, B, and C are disclosed as well as a class of coils D, E, and F and an example of a combination coil, or, for example, a combination coil comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "can," "may," "optionally," "can optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The term "ablation" or "to ablate" refers to the destruction of cellular or tissue material. Ablated cells cannot replicate and are in essence, killed cells. Ablation can be determined by, for example, live/dead staining of cells or other methods to determine the live/dead status of cells. Alternatively, ablation can be determined by measuring factors known to cause or known to indicate cell death (e.g., tissue temperature above 60° C.; presence of necrosis indicators).

A "subject" can be any mammalian subject, for example a human, dog, cow, horse, mouse, rabbit, etc. In some embodiments, the subject is a primate, particularly a human. The subject can be a male or female of any age, race, creed, ethnicity, socio-economic status, or other general classifiers. In some embodiments, the subject is a patient undergoing a tissue ablation procedure (e.g., a patient under the care of a medical professional).

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

Devices

It is understood that the devices of the present disclosure can be used in combination with the various compositions, methods, products, and applications disclosed herein.

Characteristics of ideal devices for tissue ablation include minimal invasiveness, efficient ablation of undesirable tissue, and control over the zone of ablation to avoid destroying healthy tissue. Ablation devices having these properties can ultimately result in simple, safe, and effective procedures which may avoid surgery or other more invasive procedures. However, many ablation devices contain cords and wires that complicate use of the device and present the risk of cutting or shorting the circuit if they are damaged. Many currently used ablation devices are also very bulky and frequently require integration into or onto a large cart for mobility. The disclosure herein addresses needs in the art at least by providing for a wirelessly powered tissue ablation device. The device is effective for creating a focused and adjustable zone of ablation to ablate, for example, a tumor. The device is compact, lightweight, and mobile. The entire device can be sufficiently small and compact to be positioned on a patient without discomfort, and thus does not require an operating room for use.

Disclosed herein is a wireless tissue ablation device comprising an alternating magnetic field generator; an ablation probe comprising an ablation tip; a catheter comprising an opening at a tissue insertion end and a lumen extending along a length of the catheter to the catheter opening; and a magnetic field receiving coil configured to be electrically coupled to the ablation probe; wherein at least a portion of the ablation probe is positionable within the lumen of the catheter, and wherein the ablation tip protrudes through the opening of the catheter.

An advantage of the disclosed device is the ability to power an ablation probe without the use of wires. The alternating magnetic field generator generates a magnetic field which can wirelessly induce an electrical current in the magnetic field receiving coil by electromagnetic induction. The entire device can be miniaturized or compacted such that the device can be easily portable and/or comfortably placed on a subject's body.

Figure 1B:
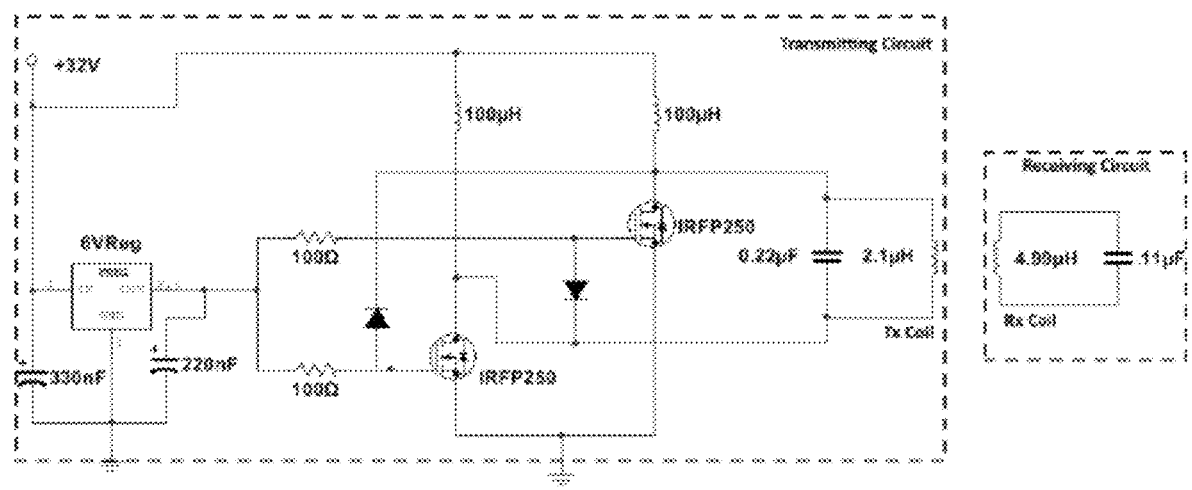
FIG. 1B is a circuit diagram showing the transmitting (Tx) and receiving (Rx) circuits.

The wireless tissue ablation device comprises an alternating magnetic field generator. Referring to FIG. 1, the alternating magnetic field generator can be represented by the non-limiting, example circuitry diagram of FIG. 1A (Tx) and FIG. 1B (Transmitting Circuit). Any magnetic field generator can be used which produces a magnetic field sufficient to induce a current in a magnetic field receiving coil and can power the disclosed ablation probe. In some embodiments, the alternating magnetic field generator comprises a magnetic field transmitting coil. In some embodiments, the alternating magnetic field generator is powered by a battery. Thus, in some embodiments, the magnetic field transmitting coil can conduct an alternating current, or in other words, oscillate. Oscillation of the magnetic field transmitting coil can produce a magnetic field, which can induce an electrical current in an appropriately positioned magnetic field receiving coil.

Figure 2:
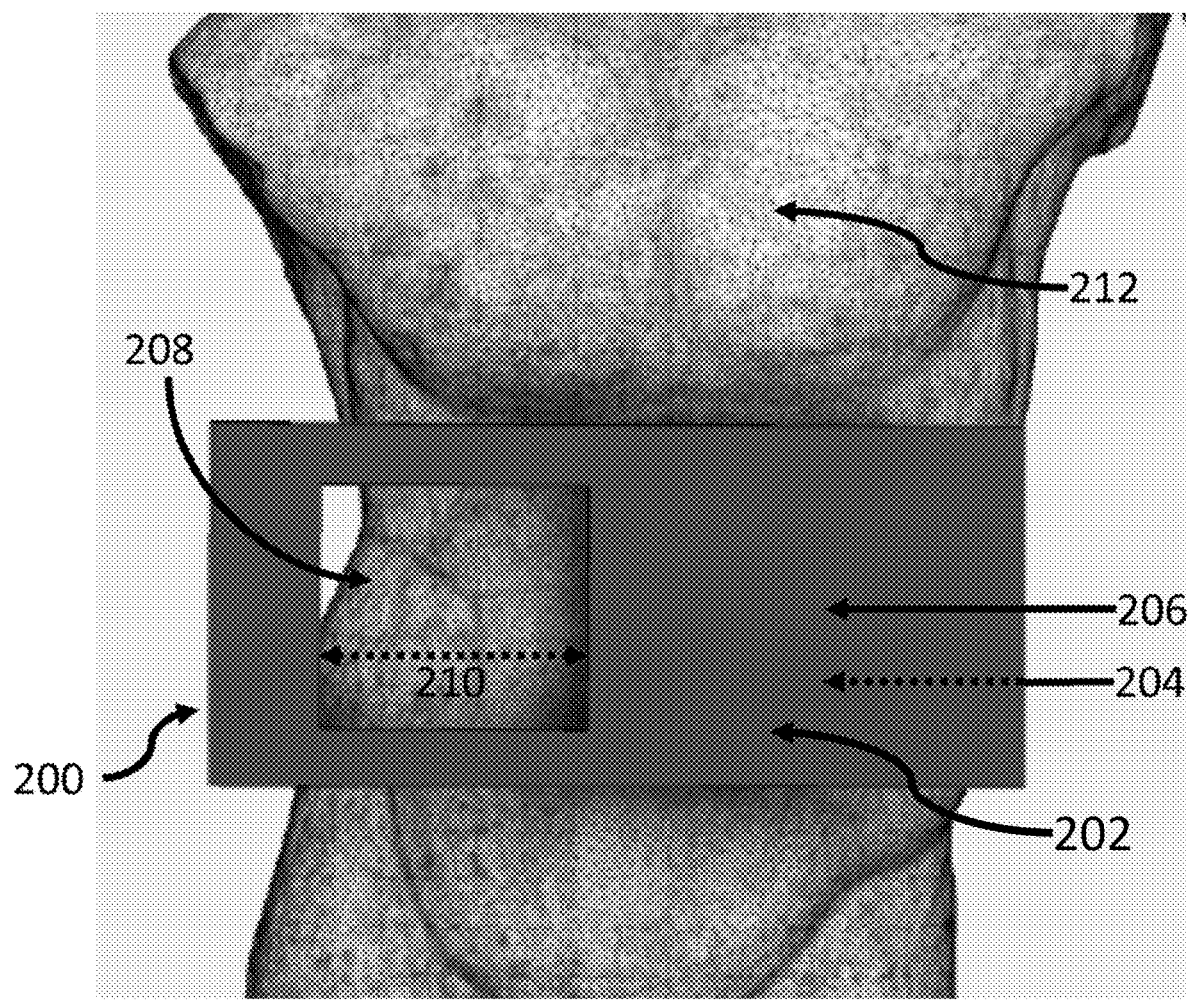
FIG. 2 is an image showing an example wireless RFA device with all electronics embedded in a housing. The hole is an area in which the ablation catheter can access the body.

Referring now to FIG. 2, the wireless tissue ablation device (200) comprises an alternating magnetic field generator which can, in some embodiments, be comprised within a housing, for example a portable housing (202). The portable housing is not limited to any particular geometric shape, but can be configured for a number of applications and/or purposes. In some embodiments, the portable housing comprises a bottom surface (204). The bottom surface of the portable housing can be configured to contact a subject (212). The portable housing can also comprise a top surface (206). In some embodiments, the portable housing further comprises an access opening (208). The access opening can extend from the top surface to the bottom surface. In some embodiments, the access opening can provide access to the subject upon positioning the portable housing on the subject. The access opening can have a width (210) through which one or more objects may be passaged.

Figure 3A:
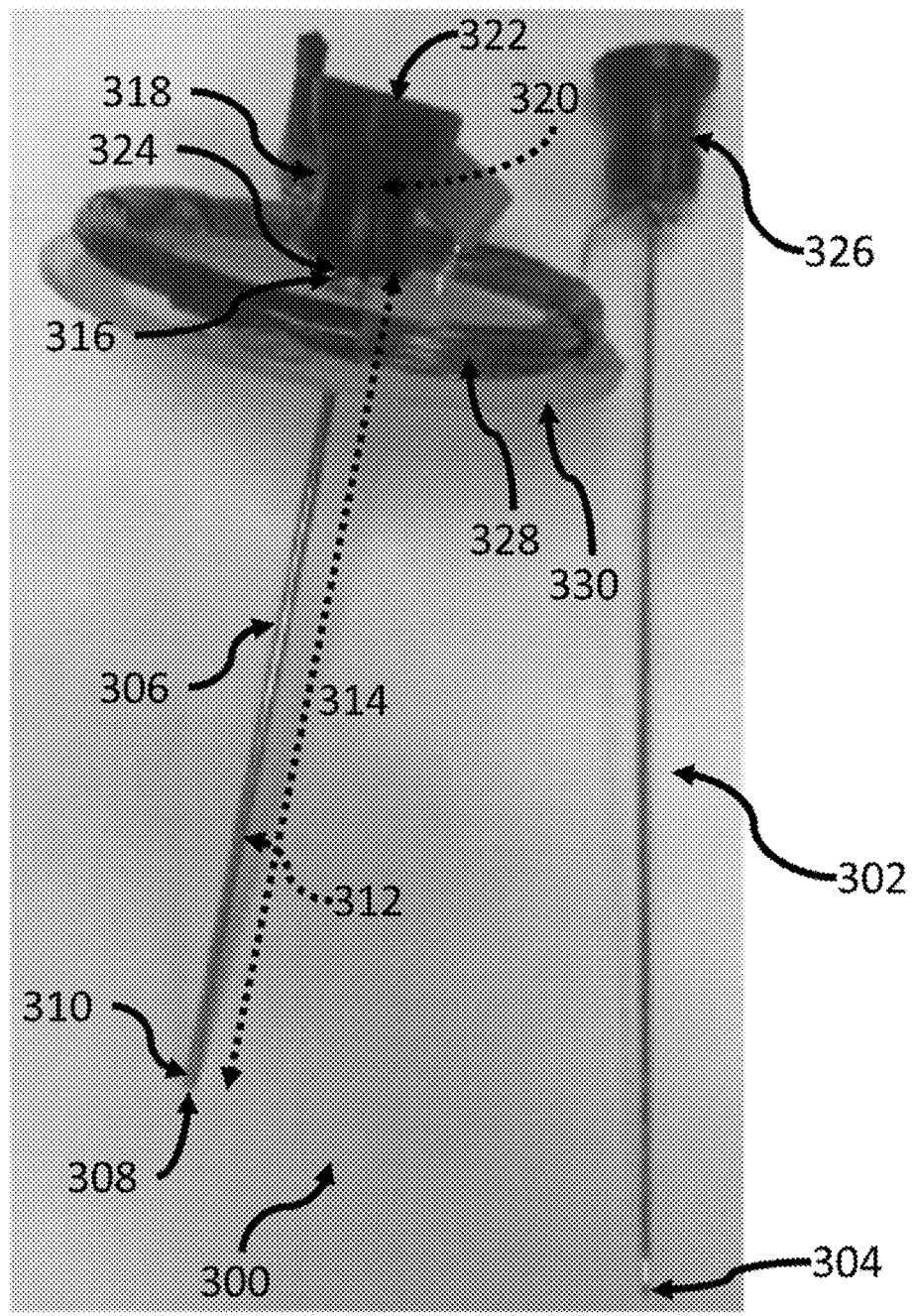
FIG. 3A shows the inside catheter next to the outside sheath and the Rx LC Circuit.

Referring now to FIG. 3A, the wireless tissue ablation device (300) also comprises an ablation probe (302) comprising an ablation tip (304). The device also comprises a catheter (306). The catheter comprises an opening (308) at a tissue insertion end (310) and a lumen (312). The lumen can extend along a length (314) of the catheter to the catheter opening. The lumen can also extend to an ablation probe insertion opening (316). In some embodiments, the device may further comprise a catheter grip (318). The catheter grip can comprise can be attached to the catheter to provide additional grip for a user when inserting or retracting the catheter from a patient. In some embodiments, the catheter grip can be a detachable knob or handle. In some embodiments, the catheter grip can further comprise a catheter grip lumen (320) which extends from a distal opening (322) to a proximal opening (324). The catheter grip lumen can, in some embodiments, linearly align with the catheter lumen such that a passageway is created from the distal opening of the catheter grip lumen to the catheter opening of the catheter. In some embodiments, the ablation probe can also comprise a probe grip (326). Similar to the catheter grip, the probe grip can provide additional grip for a user when inserting or retracting the probe in the catheter.

The device also comprises a magnetic field receiving coil (328). The magnetic field receiving coil is configured to be electrically coupled to the ablation probe. Electrical coupling of the magnetic field receiving coil to the ablation probe can occur when the ablation probe is positioned in the catheter. In some embodiments, the magnetic field receiving coil is attached to the catheter. In some embodiments, the magnetic field receiving coil is positioned on a stop barrier (330). In some embodiments, the stop barrier is an electrically insulated stop barrier. The stop barrier can be attached to the catheter or to the ablation probe. In some embodiments, the magnetic field receiving coil is attached to the ablation probe.

Figure 3B:
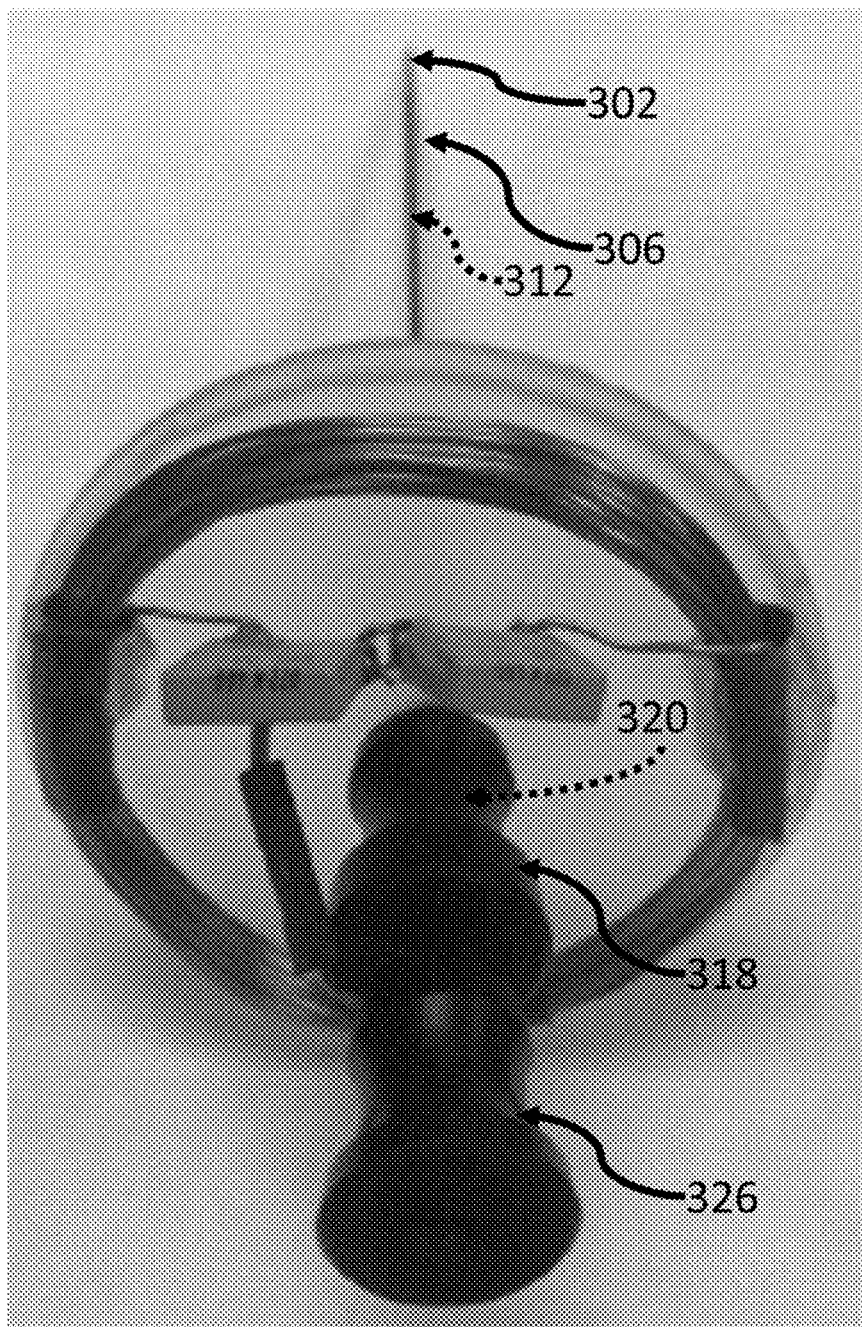
FIG. 3B shows both parts of the catheter together.

Referring now to FIG. 3B, at least a portion of the ablation probe (302) is positionable within the lumen (312) of the catheter (306). For example, the ablation probe can be slidably inserted into the catheter, and a catheter grip (318) can be attached to the catheter to secure the ablation probe in place. In embodiments comprising a catheter grip lumen (320), the ablation probe can be slidably inserted through the catheter grip (318) and into the catheter. Thus, in some embodiments, an ablation probe can be inserted through the catheter grip distal opening, the catheter grip lumen, the catheter grip proximal opening, the ablation probe insertion opening, the catheter lumen, and through the catheter opening. In some embodiments, the ablation probe comprises a probe grip (326) to facilitate easy insertion and removal of the ablation probe.

Figure 3C:
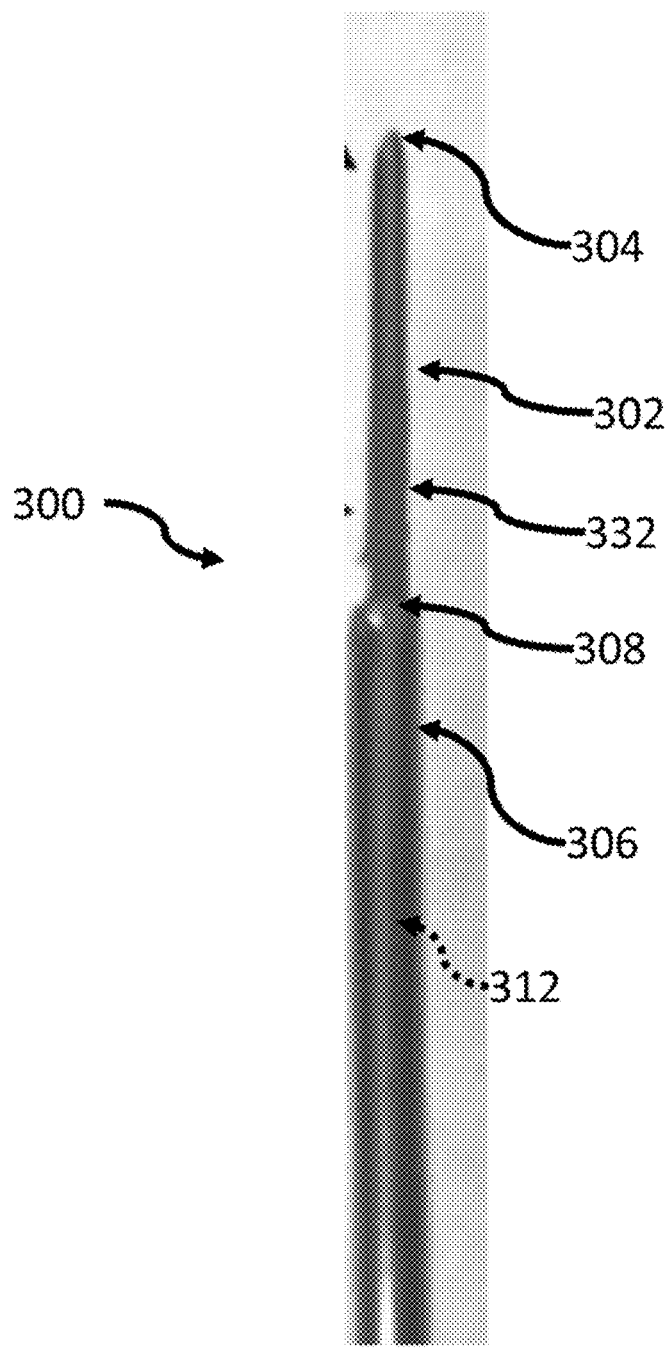
FIG. 3C shows the tip of the ablation catheter. The inside catheter is inserted into the outside sheath and the varnish insulates the inside catheter from the outside sheath.

Referring now to FIG. 3C, the ablation tip (304) protrudes through the opening (308) of the catheter (306) when the wireless tissue ablation device (300) is used for tissue ablation. This configuration can facilitate contact between the ablation tip and the tissue to be ablated. In some embodiments, the portion of the ablation probe positionable within the lumen (312) of the catheter comprises a probe outer surface electrical insulator (332). The probe outer surface electrical insulator can insulate electrical conductance in the ablation probe from the inner wall of the catheter.

The device can, in some embodiments, be configured for radiofrequency ablation. For example, the device can be configured to deliver to tissue a current ranging from about 50 kHz to about 500 kHz, from about 100 kHz to about 400 kHz, from about 150 kHz to about 300 kHz, or from about 200 kHz to about 250 kHz. In some embodiments, the device can be configured to deliver to tissue a current ranging from about 200 kHz to about 240 kHz, from about 205 kHz to about 235 kHz, from about 210 kHz to about 230 kHz, from about 215 kHz to about 225 kHz, or at about 220 kHz.

The device can, in some embodiments, be configured for microwave ablation. For example, the device can be configured to deliver to tissue a current ranging from about 300 MHz to about 300 GHz, from about 500 MHz to about 100 GHz, from about 750 MHz to about 50 GHz, or from about 900 MHz to about 10 GHz.

As discussed, the alternating magnetic field generator generates a magnetic field which can wirelessly induce an electrical current in the magnetic field receiving coil by electromagnetic induction. One example method to optimize the power received by the magnetic field receiving coil is by resonant induction coupling (RIC). RIC is a form of electromagnetic induction in which the transmitting coil and the receiving coil resonate at similar or identical frequencies. The transmitting coil and the receiving coil are coupled when each coil resonates at a frequency which is similar or identical to the other such that power transfer from the transmitting coil to the receiving coil is enhanced.

In some embodiments, the magnetic field transmitting coil and the magnetic field receiving coil are configured to resonate at a frequency from about 200 kHz to about 240 kHz. In some embodiments, the magnetic field transmitting coil and the magnetic field receiving coil are configured to resonate at a frequency from about 205 kHz to about 235 kHz, from about 210 kHz to about 230 kHz, from about 215 kHz to about 225 kHz, or at about 220 kHz.

In some embodiments, the magnetic field transmitting coil and the magnetic field receiving coil can be configured to have oscillation frequencies within 20 kHz of each other, thereby resonance coupling the magnetic field receiving coil and the magnetic field transmitting coil. Such an embodiment can be described as coils which are coupled at a resonance frequency X +/−20 kHz. In some embodiments, the magnetic field transmitting coil and the magnetic field receiving coil can be configured to have oscillation frequencies within 15 kHz, 10 kHz, 5 kHz, 4 kHz, 3 kHz, 2 kHz, or 1 kHz or less of each other. In some embodiments, the magnetic field transmitting coil and the magnetic field receiving coil are configured to be coupled at substantial identical frequencies.

In some embodiments, the alternating magnetic field generator is comprised of easily accessible and exchangeable parts. In some embodiments, the alternating magnetic field generator can be positioned within a housing. A housing can encase the components of the alternating magnetic field generator to achieve compaction of the device, to protect the encased components, to facilitate portability, and to safeguard users and subjects from the electrical or sharp components therein. The housing can be made of any suitable materials such as metal, plastic, rubber, polymer, etc. In some embodiments, the housing may be coated with a rubber or a polymer to increase comfort when contacting the housing to the subject's body.

Another advantage of encasing the alternating magnetic field generator in a portable housing is the ability to position the alternating magnetic field generator in desirable locations. The amount of power transferred wireless increases as the distance between the transmitting and receiving coils decreases. Thus, it is desirable to position an alternating magnetic field generator comprising a magnetic field transmitting coil closely to a magnetic field receiving coil (e.g., a receiving coil attached to the disclosed catheter). Because the catheter and ablation probe are typically contacted to or positioned within a subject undergoing an ablation procedure, it would be advantageous to position the alternating magnetic field generator on or near the subject. Thus, the portable housing encasing the alternating magnetic field generator can be positioned near (e.g., adjacent) or on a subject undergoing an ablation procedure, or alternatively, be attached to the subject (e.g., by straps, belts, sleeves, or other similar devices). In some embodiments, the bottom surface of the portable housing can be elongated. For example, the portable housing can be positioned on a subject by contacting the bottom surface to the subject, wherein the portable housing rests on the body of the subject. In other instances, the portable housing can be positioned on a surface (e.g., a table, tray, or cart) or can be positioned partially on a subject and partially on another surface.

In such embodiments, weight of the entire portable housing comprising an alternating magnetic field generator can be a factor for subject (e.g., patient) comfort. In some embodiments, the weight of the entire portable housing comprising an alternating magnetic field generator can be 25 pounds or less, 20 pounds or less, 15 pounds or less, or 10 pounds or less. In some embodiments, the weight of the entire portable housing comprising an alternating magnetic field generator can be 9, 8, 7, 6, 5, 4, or 3 pounds or less.

In some embodiments, the alternating magnetic field generator or the portable housing comprising an alternating magnetic field generator can be positioned next to a catheter insertion site where an ablation procedure is to be performed. In such embodiments, the catheter can be inserted into the catheter insertion site adjacent the alternating magnetic field generator. In some embodiments, the portable housing can comprise a top surface, a bottom surface, and an access opening extending from the top surface to the bottom surface. Thus, the access opening can provide access to the subject's body upon positioning the portable housing on the subject. The access opening desirably has a width sufficient to passage one or more objects. In some embodiments, the access opening has a width sufficient to allow passage of the catheter through the portable housing to the subject's body. The access opening can, but need not, have a width sufficient to allow passage of a stop barrier or a magnetic field receiving coil. Alternatively, the access opening can have a width sufficient to allow passage of a catheter but not larger, bulkier components (e.g., greater than a few inches in width). In some embodiments, the access opening of the portable housing has a width of 5, 4, 3, 2, or 1 inches or less. The access opening can be partially or fully defined by the portable housing. For example, the access opening can be fully within the portable housing and thus defined on all lateral sides by the portable housing. Alternatively, the access opening can be partially defined by a cutaway portion of a side of the portable housing.

The coils used in the magnetic field transmitting coil and the magnetic field receiving coil can be the same or different. The coils can have any suitable thickness or number of coiling (e.g., turns) sufficient for transmitting and receiving power. The coils can be made of any suitable electrically conductive material, such as copper, aluminum, silver, gold, tungsten, metal alloy, or other suitable materials.

The catheter can be formed of any suitable rigid or flexible materials. The catheter can be, but need not be, comprised of electrically conductive materials, for example to complete a conductance circuit during ablation. The catheter can have adjustable lengths or, alternatively, can comprise a series of two or more exchangeable catheters having differing lengths to match the depth of the tissue within the subject to be ablated. In some embodiments, the catheter has a length of 12 inches or less. In some embodiments, the catheter has a length of 10, 9, 8, 7, 6, 5, 4, 3, 2, or 1 inches or less.

The ablation probe can be any element which can be positionable within the catheter and can deliver power to the ablation tip. The term "probe" is understood to encompass any probe, needle, catheter, wire, filament, or other element usable to deliver power to the ablation tip. The ablation probe can be formed of any suitable rigid or flexible materials. The ablation probe is generally comprised of electrically conductive materials (e.g., copper, aluminum, metal alloys, etc.) but can contain non-conductive materials as well. The ablation probe can be configured to be electrically coupled to the magnetic field receiving coil to receive power from the receiving coil. For example, the ablation probe can comprise a lead which connects to a suitable lead of the magnetic field receiving coil.

The ablation probe generally has an outer thickness or diameter which is smaller than the inner thickness or diameter of the catheter defining the catheter lumen. Thus, the ablation probe is positionable within the lumen of the catheter. For example, the ablation probe can slide through the ablation probe insertion opening, through the catheter lumen, and through the catheter opening, thereby protruding out from the catheter opening and capable of directly contacting tissue to be ablated. The ablation probe can have adjustable lengths or, alternatively, can comprise a series of two or more exchangeable ablation probes having differing lengths to match the depth of the tissue within the subject to be ablated. In some embodiments, the ablation probe has a length of 12 inches or less. In some embodiments, the ablation probe has a length of 10, 9, 8, 7, 6, 5, 4, 3, 2, or 1 inches or less.

The ablation probe comprises an ablation tip, which can have any suitable shape or size. In some embodiments, the ablation tip can be tapered or sharp, for example to puncture tissue, or can be blunt, rounded, or irregular in shape.

In some embodiments, the ablation probe can be electrically insulated to prevent shunting to the catheter or other components. For example, the ablation probe can comprise a probe outer surface electrical insulator, which can be comprised of any suitable electrically insulating material (e.g., rubber, polymer, resin, varnish, Teflon, glass, etc.). In some embodiments, the probe outer surface electrical insulator can be a material brushed or painted onto the outer surface of the ablation probe (e.g., a paint or varnish). The probe outer surface electrical insulator does not cover the entire ablation probe. In particular, some or all of the ablation tip is not covered by the probe outer surface electrical insulator so that the ablation tip can deliver current during an ablation procedure.

Methods of Use

Also provided herein are methods of ablating a target tissue in a subject, the methods comprising positioning in the subject a catheter comprising an opening at a tissue insertion end and a lumen; contacting the target tissue with an ablation tip of an ablation probe, wherein at least a portion of the ablation probe is positioned within the lumen of the catheter, and wherein the ablation tip protrudes through the opening of the catheter; generating a magnetic field from an alternating magnetic field generator to wirelessly induce a current in a magnetic field receiving coil electrically coupled to the ablation probe; and electrically energizing the ablation tip, thereby ablating the target tissue.

The methods can use any herein disclosed ablation device, and it is expressly understood that the device(s) can be modified by those of ordinary skill within the art for purposes of the methods described herein.

The catheter can be positioned in a subject according to procedures known in the art. Typically, a small incision is made in the skin, through which the catheter can be inserted. For ablation of surface-exposed tissue (e.g., a skin cancer), the positioning of the catheter in the subject can simply comprise contacting the ablation tip to the surface-exposed tissue to be ablated without incising the skin.

During ablation, the target tissue is contacted with the ablation tip. The ablation tip can be contacted with the surface of the target tissue or, alternatively, the ablation tip can be inserted within the target tissue.

The ablation probe can be electrically connected to receive power from the magnetic field receiving coil, which in turn receives power from the alternating magnetic field generator. Thus, a magnetic field is generated from an alternating magnetic field generator to wirelessly induce a current in a magnetic field receiving coil electrically coupled to the ablation probe. The magnetic field can be generated by powering the alternating magnetic field generator with a power source. To reduce or eliminate the number of wires extending external to the device, the power source can be a battery, which in some embodiments can be positioned within a housing encasing the alternating magnetic field generator.

As the ablation probe is electrically coupled to the magnetic field receiving coil, the ablation tip can be electrically energized upon wirelessly inducing a current in the magnetic field receiving coil. Electrically energizing the ablation tip can thereby deliver current to the target tissue, thereby ablating the target tissue.

In some embodiments, the method can comprise positioning the portable housing on or near the subject. In some embodiments, the methods comprise positioning the portable housing on the subject adjacent to a catheter insertion point. For example, the methods can comprise positioning the portable housing within 24, 18, 12, 10, 9, 8, 7, 6, 5, 4, 3, 2, or 1 inches or less of the catheter insertion point. In some embodiments in which the portable housing comprises an access opening, the portable housing can be positioned on the subject such that the access opening permits access of a device user to the catheter insertion point.

In some embodiments, the magnetic field receiving coil can be coupled or attached to the catheter. Thus, as the catheter is positioned in the subject, the magnetic field receiving coil can be positioned adjacent or above the catheter insertion point. In embodiments in which the alternating magnetic field generator is positioned adjacent or over the catheter insertion point, a magnetic field receiving coil coupled to a catheter inserted into the subject can thus be positioned within close proximity of the alternating magnetic field generator. In such embodiments, slidably inserting the catheter into the subject can move the magnetic field receiving coil closer to the subject's body and thus, closer to the alternating magnetic field generator. In some embodiments, the magnetic field receiving coil is positioned within 24, 18, 12, 10, 9, 8, 7, 6, 5, 4, 3, 2, or 1 inches or less of the alternating magnetic field generator.

In some embodiments, the methods can further comprise setting or adjusting the oscillation frequency of the magnetic field transmitting coil, the magnetic field receiving coil, or both. The methods can comprise adjusting the coils to any herein disclosed oscillation frequency suitable for the particular coils.

In some embodiments, the methods can comprise ablating tissue using radiofrequency ablation. For example, the methods can comprise setting or adjusting the device to deliver to tissue a current ranging from about 50 kHz to about 500 kHz, from about 100 kHz to about 400 kHz, from about 150 kHz to about 300 kHz, or from about 200 kHz to about 250 kHz. In some embodiments, the methods can comprise setting or adjusting the device to deliver to tissue a current ranging from about 200 kHz to about 240 kHz, from about 205 kHz to about 235 kHz, from about 210 kHz to about 230 kHz, from about 215 kHz to about 225 kHz, or at about 220 kHz.

In some embodiments, the methods can comprise ablating tissue using microwave ablation. For example, the methods can comprise setting or adjusting the device to deliver to tissue a current ranging from about 300 MHz to about 300 GHz, from about 500 MHz to about 100 GHz, from about 750 MHz to about 50 GHz, or from about 900 MHz to about 10 GHz.

In some embodiments, the methods can comprise setting or adjusting the magnetic field transmitting coil and the magnetic field receiving coil to have oscillation frequencies within 20 kHz of each other, thereby resonance coupling the coils. In some embodiments, the methods can comprise setting or adjusting the magnetic field transmitting coil and the magnetic field receiving coil to have oscillation frequencies within 15 kHz, 10 kHz, 5 kHz, 4 kHz, 3 kHz, 2 kHz, or 1 kHz or less of each other. In some embodiments, the methods can comprise setting or adjusting the magnetic field transmitting coil and the magnetic field receiving coil to be coupled at substantial identical frequencies.

Tissue ablation procedures can be more safely and reliably performed depending in part on consistency in the power supplied to the ablation probe. In some embodiments, the method further comprises coupling a resonance converter to the magnetic receiving coil. In such embodiments, the resonance converter can adjust the current to facilitate resonance coupling between the magnetic field receiving coil and the magnetic field transmitting coil. In some embodiments, the resonance converter increases the duration which the magnetic field receiving coil and the magnetic field transmitting coil are coupled. In some embodiments, the resonance converter decreases the difference in oscillation frequencies between the magnetic field receiving coil and the magnetic field transmitting coil.

The alternating magnetic field generator has a power output can have a power output sufficient to power an ablation probe in a tissue ablation procedure. In some embodiments, the alternating magnetic field generator has a power output of at least 20 W. In some embodiments, the alternating magnetic field generator has a power output of at least 50 W, at least 100 W, at least 150 W, at least 200 W, at least 250 W, at least 300 W, or at least 500 W.

The ablation probe has a power output which depends in part on the power output of the magnetic field transmitting coil and the distance between the magnetic field receiving coil and the magnetic field transmitting coil. The ablation probe has a power output sufficient to perform a tissue ablation procedure. In some embodiments, the ablation probe has a power output of at least 20 W. In some embodiments, the alternating magnetic field generator has a power output of at least 50 W, at least 100 W, at least 150 W, at least 200 W, at least 250 W, at least 300 W, or at least 500 W.

The target tissue can be any tissue capable of being ablated. In some embodiments, the target tissue is a mammalian tissue. In some embodiments, the target tissue is a human tissue. In some embodiments, the target tissue comprises one or more of liver, pancreatic, pulmonary, cardiac, epithelial, gall bladder, bone, cartilage, neurological, venous/arterial, stomach or gastrointestinal, bladder, renal, muscular, glandular, mesentery, ovarian, uterine, genital, mammary, lymphatic, or splenic tissues. In some embodiments, the target tissue comprises a tumor (e.g., within liver tissue). In some embodiments, the target tissue comprises a malignancy.

Many parameters of the devices and methods can be varied according to the nature of the ablation procedure and/or tissue to be ablated. For example, the methods can comprise ablating the tissue for longer or shorter periods of time, supplying increased or decreased amounts of power to the ablation probe (by, for example, altering the power supplied to the alternating magnetic field generator, altering the distance between the magnetic field transmitting coil and the magnetic field receiving coil, or both), altering the oscillating frequencies of the coils, or other parameters. Generally, a longer duration of ablation will ablate more tissue. Similarly, applying increased power to the ablation probe will generally ablate more tissue. Different tissues can also have different resistances, and thus the parameters of the ablation procedure can be adjusted accordingly.

The methods can comprise ablating the tissue for any time sufficient to achieve the desired results. In some embodiments, the target tissue is ablated for 60 minutes or less. In some embodiments, the target tissue is ablated for 45 minutes or less, 30 minutes or less, 20 minutes or less, 15 minutes or less, 10 minutes or less, 5 minutes or less, 4 minutes or less, 3 minutes or less, or 2 minutes or less. In some embodiments, the target tissue is ablated for 60 seconds or less, 45 seconds or less, 30 seconds or less, 20 seconds or less, 10 seconds or less, or 5 seconds or less.

The methods can comprise ablating a zone of target tissue sufficient to achieve the desired results. In some embodiments, the zone of target tissue is sufficient to ablate a target tissue (e.g., a tumor). In some embodiments, the zone of target tissue avoids ablating healthy tissue. In some embodiments, the method ablates a zone of target tissue having a width of 50 mm or less, 40 mm or less, 30 mm or less, 20 mm or less, or 10 mm or less. In some embodiments, the method ablates a zone of target tissue having a width of 5 mm or less, 4 mm or less, 3 mm or less, 2 mm or less, or 1 mm or less.

The methods can comprise increasing the temperature of the target tissue to a temperature sufficient to ablate a target tissue. A sufficient temperature for ablation can vary depending on the target tissue type. In some embodiments, the methods increase the temperature of the target tissue to a temperature of at least 45° C., at least 50° C., at least 55° C., at least 60° C., at least 65° C., at least 70° C., or at least 75° C.

The methods can include any form of delivering current to perform an ablation procedure. In some embodiments, the current can follow a path from the ablation tip, to the target tissue, and to an electrical sink. In some embodiments, the electrical sink can be an electrode, the catheter, the target tissue, non-target tissue of the subject, or a ground. In some embodiments, the current can be an alternating current and thus can be bidirectional. Generally, an alternating current can induce ion flow, which can generate heat in the target tissue.

In embodiments of the method comprising use of a portable device, the methods can be performed in a wide array of locations. In some embodiments, the method is performed in a hospital or clinic. In some embodiments, the method is performed in an operating room, an emergency room, a clinical observation room, an in-patient hospital room, an out-patient clinic, or a veterinary clinic. In some embodiments, the method is performed outside of an operating room.

In some embodiments, the method further comprises positioning a cooling element and a thermal coupler in the lumen of the catheter to provide thermodynamic information during the method. In some embodiments, the method further comprises coupling a device to the ablation probe to control ablation time. In some embodiments, a device to control ablation time can be a microcontroller, analog circuit, computer, stop watch, or other timing device.

Also provided herein are methods of treating a subject, the methods comprising positioning in the subject a catheter comprising an opening at a tissue insertion end and a lumen; contacting the target tissue with an ablation tip of an ablation probe, wherein at least a portion of the ablation probe is positioned within the lumen of the catheter, and wherein the ablation tip protrudes through the opening of the catheter; generating a magnetic field from an alternating magnetic field generator to wirelessly induce a current in a magnetic field receiving coil electrically coupled to the ablation probe; and electrically energizing the ablation tip, thereby treating the subject.

The methods can comprise any herein disclosed devices, methods, and/or parameters of methods.

In some embodiments, the subject has a condition or disease. In some embodiments, the condition or disease comprises a tumor, cardiac arrhythmia, dermatological defect, varicose vein(s), obstructive sleep apnea, pain, Barret's esophagus, or other such conditions for which exposure to an ablation probe could be beneficial.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. These examples are not intended to exclude equivalents and variations of the present invention which are apparent to one skilled in the art. Unless indicated otherwise, temperature is 20° C. or is at ambient temperature, and pressure is at or near atmospheric. There are numerous variations and combinations of process conditions that can be used to optimize product quality and performance. Only reasonable and routine experimentation will be required to optimize such process conditions.

Example 1

Liver radiofrequency ablation (RFA) is a minimally invasive medical procedure in which tumors are ablated in the body with electrical current. Current methods of RFA use several cords and wires that complicate the procedure and present the risk of cutting or shorting the circuit if they are damaged. Disclosed herein are devices and methods for wireless RFA using electromagnetic induction. The transmitting and receiving coil were coupled to resonate at the same frequency to facilitate optimal ablation power output. The receiving coil was connected to two separated electrodes on a catheter to flow current to the targeted tissue. The device was tested by using an in vivo animal tissue having similar resistive characteristics to the human liver. The experimental ablation was performed with monitored temperature; the tissue around the catheter was heated to cytotoxic temperatures thereby causing cellular death in those areas. Thus, the devices disclosed herein can perform RFA wirelessly with electromagnetic induction.

Methods

Electromagnetic induction was used to power an ablation catheter wirelessly. A coil of wire can oscillate with sufficient power to produce a magnetic field and induce an electrical current on the receiving coil centimeters away. The Law of Biot-Savart (Formula 1) was applied to determine the strength of the magnetic field at any height from the center point of the transmitting coil. Since the coil is a symmetrical circle, the surface integral about the line equals one and the equation reduces to a function of current and circle radius.

$$B = \frac{\mu_0 I}{4\pi R^2} \oint dL = \frac{\mu_0 I}{2R} \qquad \text{Formula 1}$$

Positioning another coil of wire within this switching magnetic field generated an electrical current that could be directed through a tumor in the body. The distance between the transmitting coil and the receiving coil can vary based on the position of the tumor in the patient's body. Therefore, an efficient method to capture the highest amount of energy on the receiving circuit is to couple both coils at one resonant frequency.

Magnetic resonance is the theory that relates the frequency of an resonant circuit (LC circuit) to the power produced. For every LC circuit, there is a specific resonant frequency in which the circuit performs optimally. As the LC circuit reaches its resonant frequency, the total impedance of the circuit approaches zero and the power output increases. The resonant frequency can be determined with the resonance formula (Formula 2) which expresses frequency in terms of circuit inductance and capacitance ((J. I. Agbinya, *Wireless power transfer*. River Publishers, 2015).

$$f_{resonant} = \frac{1}{2\pi\sqrt{LC}} \qquad \text{Formula 2}$$

A. Transmitting Circuit

A transmitter was equipped with an oscillating circuit and resonating coil (FIG. 1B). The circuit oscillated at about 215 kHz and generated a sine wave of 180 Vpp. The circuit was powered by a 32 VDC power supply and required 1.5 amps to generate the sine wave without a load on the receiving side. The current transmitting coil was 12 cm in diameter, had 3 turns, and had parallel capacitance to tune its resonant frequency.

The electrical components and transmitting (Tx) coil was embedded into a portable wireless RFA generator (FIG. 2). The electronics were powered by a battery and thus, the entire system was wireless. A square hole was cut into the RFA generator where the receiving catheter can operate. Constricting all the electronics to this enclosure can provide a clean workspace for a user (e.g., an operating surgeon).

B. Receiving Circuit

The catheter was constructed with two parts—an inside catheter and an outside sheath. The inside catheter had a diameter of 0.85 mm and the outside sheath had a diameter of 1.75 mm. Each were connected to one side of the receiving coil (FIG. 1A). The receiving coil was coupled at the same resonant frequency to receive optimal voltage. First, the inductor coil was designed to be 6 cm, which was half the diameter of the transmitting coil. Then a capacitor was added to couple the transmitting coil and receiving coils using Equation (2).

The inside catheter was coated with insulating varnish to prevent the two parts from touching and shorting the circuit (FIG. 3C). The base of the catheter was not coated so that a wire could connect to the receiving coil. A 1 mm length of the tip of the catheter was also not coated to flow current through the tissue and back to the outside sheath (FIG. 3).

Results

Tests were performed to demonstrate the function of the device. First, the receiving power was measured as the catheter moved deeper into the skin. Then, ablation was performed to observe heat dissipation through sample tissue.

B. Liver Ablation

The catheter device was used to ablate tissue within the body. A pig liver was ablated to simulate the functionality of the device.

Figure 4:
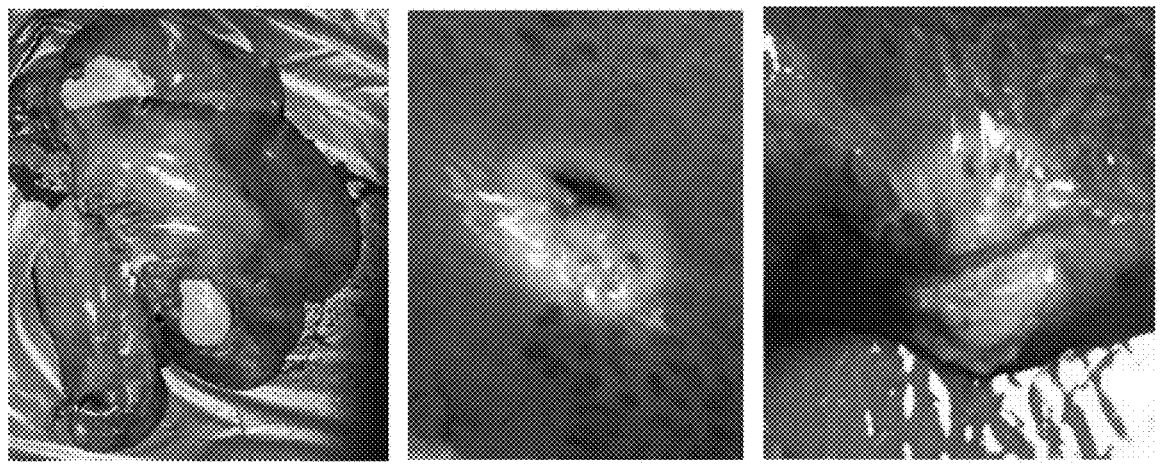
FIG. 4 is a set of images of results of catheter ablation on a pig liver. The left panel shows he liver before ablation. The middle panel shows the insertion point on the ablated liver. The right panel shows a cross section of the ablation zone. The ablation sphere is approximately 20 mm wide.
Figure 5:
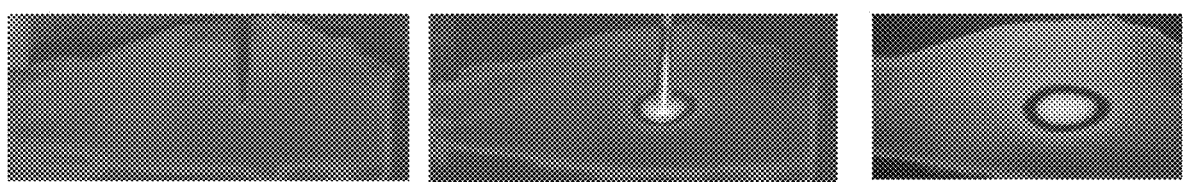
FIG. 5 is a set of images showing thermal results of catheter ablation on a pig liver. The left panel shows the catheter inserted before ablation. The middle panel shows the catheter ablating the liver. The white spot was the hottest point (about 102° C.) and the surrounding colored area had a temperature as low as 64° C. The right panel shows a liver after ablation with an approximately 20 mm ablation area.

For each ablation area tested, the catheter was inserted and ablation proceeded for 60 seconds. The catheter was positioned in the center of the cutaway portion of the generator (e.g., the access opening) and inserted to a depth of 10-12 cm. The temperature at the insertion points ranged from 64° C. to 102° C., depending on the power received from the transmitting coil. Using visual (FIG. 4) and thermal (FIG. 5) results, it was determined that the catheter could ablate a 5 mm sphere around the tip.

Discussion

A device was developed to wirelessly transfer energy to the tip of an ablation catheter. A transmitting coil was resonantly coupled with a receiving coil connected to separate parts of the catheter. The catheter was used to perform an ablation procedure on a pig liver. The catheter generated heat through the liver, which was cytotoxic to the liver tissue within a 5 mm area.

Performing thermal ablation wirelessly is demonstrated herein and is a desirable alternative to traditional wired approaches. The device can also include a microcontroller to monitor and control the ablation time. The device can also include a receiving coil smaller in diameter to make the catheter easier to hold. A cooling element and thermal couple can also be integrated in the catheter design to promote well-controlled RFA.

Example 2: Developing a Radiofrequency Tumor Ablation System with Wirelessly Powered Catheter Radiofrequency ablation (RFA) is a medical procedure where tumors are heated in the body with electrical current. RFA procedures are common amongst patients that cannot go have surgery and those looking for less invasive procedures. Current methods of RFA use several cords and wires that complicate the procedure and present the risk of cutting or shorting the circuit if they are damaged. A wireless RFA technique has been presented and outlined with the use of electromagnetic induction. The transmitting and receiving coil were coupled to resonate at the same frequency to ensure the highest power output. The receiving coil was connected to two insulated electrodes on a catheter which allow the current to flow to the targeted tissue. The prototype system was tested by using ex vivo bovine tissue which has similar characteristics to human tissue. The maximum received power was 15 W±2 W where an average maximum efficiency of 63.27% was recorded. The system was also able to ablate up to a 2 cm ablation zone. This proved the concept of performing RFA wirelessly with electromagnetic induction.

Methods

Inductive power transfer theory was used to wirelessly deliver power to the ablating electrodes. The Ampere-Maxwell Law states that electrical current flowing through a coil of wire creates a magnetic field around that wire. In addition, when that electrical current alternates in the wire, there will be an alternating magnetic field (eq.1) (Agbinya J I (2015); Kim K Y (2012); Stielau O H (2000); William B T (1995)).

$$\oint \vec{B} \cdot d\vec{l} = \mu_0 \left( I_{enc} + \varepsilon_0 \frac{d}{dt} \int_S \vec{E} \circ \hat{n} da \right) \quad (1)$$

The Law of Biot-Savart (2) is applied to determine the strength of that magnetic field at any height from the center point of the transmitting coil. Since the coil used is a symmetrical circle the surface integral about the line equals one and the equation reduces to a function of current and circle radius (Agbinya J I (2015); Kim K Y (2012); Stielau O H (2000); William B T (1995).

$$B = \frac{\mu_0 I}{4\pi R^2} \oint dL = \frac{\mu_0 I}{2R} \quad (2)$$

Faraday's Law of Induction states that an electromotive force will be induced on a coil of wire placed into a changing magnetic field. This law is representing the relationship between the strength of the magnetic field (flux), the area of the coil and the number of turns in that coil (eq. 3) (Agbinya J I (2015); Kim K Y (2012); Stielau O H (2000); William B T (1995).

$$\varepsilon = -N \frac{\Delta \Phi_B}{\Delta t} \quad (3)$$

The frequency of the oscillations can be modified by changing the inductance of the coil or the capacitance of its tuning capacitor in the LC tank circuit. The receiving coil has a similar LC tank circuit to the transmitting circuit. The inductors and capacitor are tuned to be in resonance with each other. Magnetic resonance relates the operating frequency to the values of the capacitor and inductor used. When the LC circuit operates at this the resonant frequency its reactance is its highest and its impedance is at its lowest point. Therefore, the power at the resistive load will high. The formula to determine the resonant frequency in this parallel tank circuit is shown in equation 4 (Agbinya J I (2015); Kim K Y (2012); Stielau O H (2000); William B T (1995).

$$f_{resonant} = \frac{1}{2\pi \sqrt{LC}} \quad (4)$$

Figure 6:
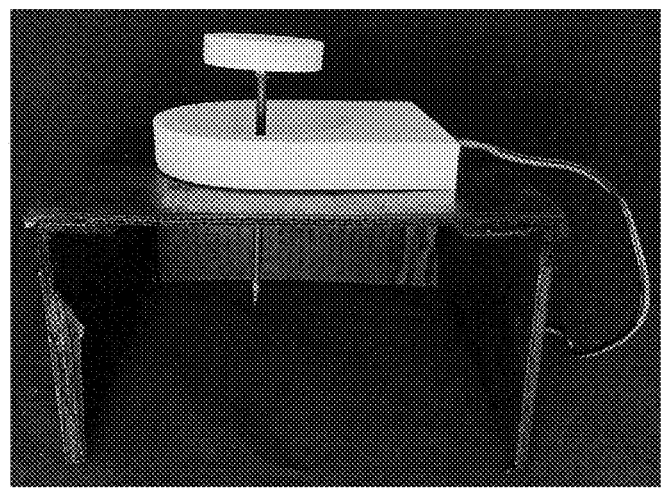
FIG. 6 shows a diagram of the transmitting (TX) and receiving (RX) configuration.

The ablation system is comprised of two parts: the ablation generator which has an oscillating circuit and transmitting coil. Then, the wireless catheter has the receiving coil and the catheter that is intended to be inserted in the body and ablate tissue. The ablation generator creates a magnetic field while the wireless catheter has a coil of wire that is placed into that field. FIG. 6 shows how the two parts of the system are used together.

Ablation Generator

Figure 7:
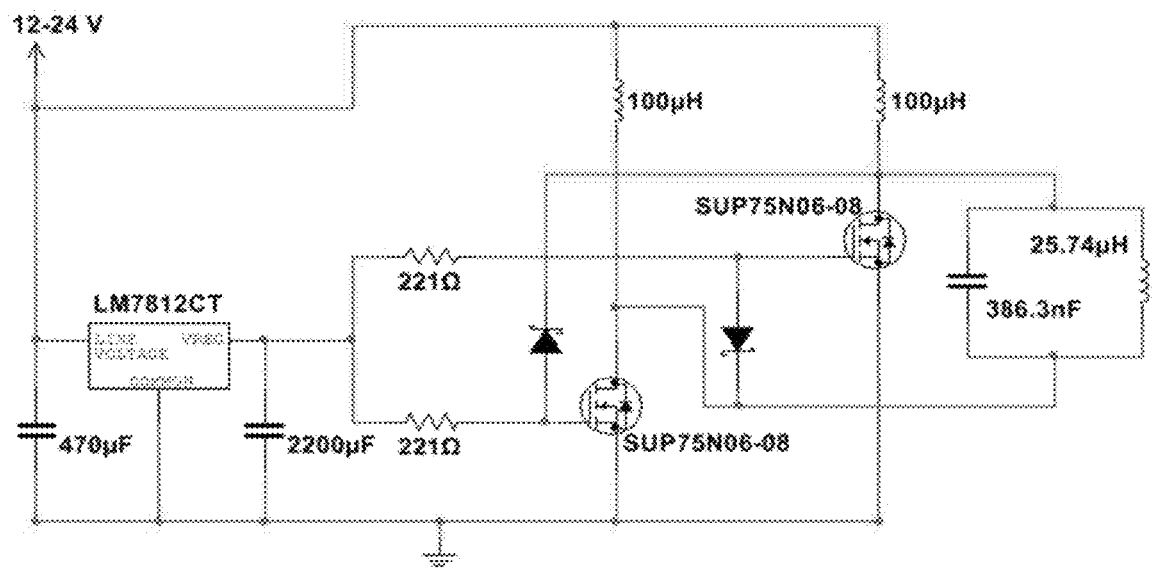
FIG. 7 shows a circuit diagram of the transmitting (TX) circuit.
Figure 8:
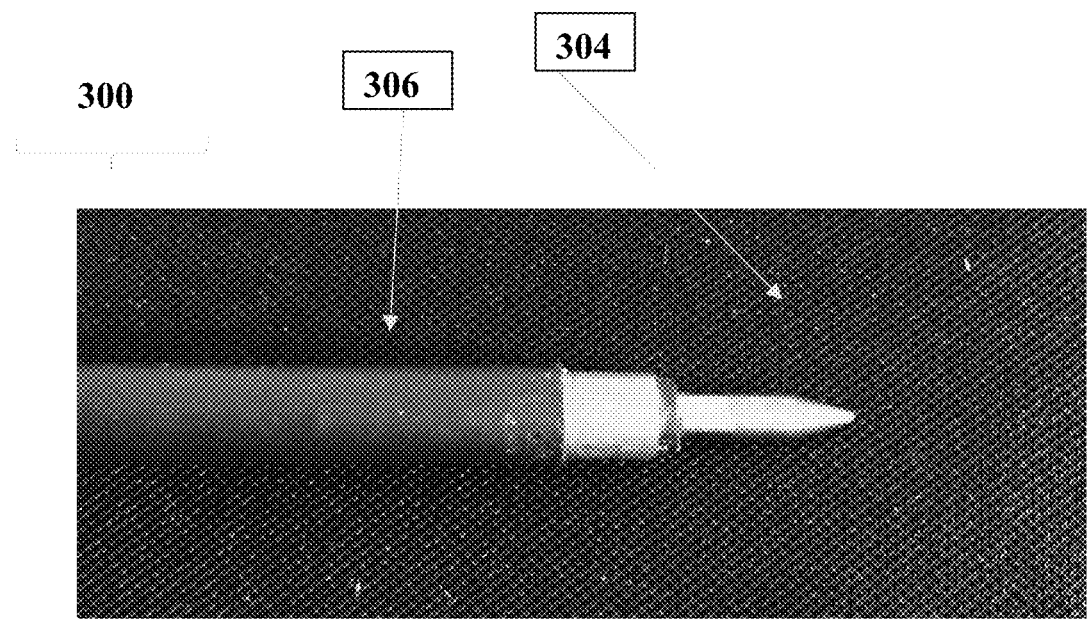
FIG. 8 shows the tip of the ablation catheter.

The ablation generator uses an amplification circuit to create an alternating current through a coil to create an alternating magnetic field. A modified Royer amplifier was used to create a medium power alternating current. This circuit amplifies the natural oscillating feedback from the LC tank circuit to create a strong magnetic field through the inductor (Costanzo et al. 2013; Mastri et al. 2012). FIG. 7A shows the diagram of the circuit used to amplify the oscillations of the tank.

The circuit is powered from a 12-24V adjustable power supply with a maximum DC current of 2.5-amps. The LC tank circuit is designed in a parallel configuration with its characteristics defined in Table 1. With equation 4 and the values of the LC tank circuit, a frequency of 50.5 kHz is calculated. This value was validated in practice as an oscillating frequency of 50-55 kHz was observed.

TABLE 1

| TX Tank Circuit Characteristics | |
| --- | --- |
| Inductance | 25.74 µH |
| Capacitance | 386.3 nF |
| Coil Diameter | 10-cm |
| Coil Turns | 12 |

Wireless Catheter

While the ablation generator produces an oscillating magnetic field, the receiving coil connected to the wireless catheter is placed within those flux lines and a voltage is induced (eq. 3). The receiving LC tank circuit is half the diameter of the transmitting and has a parallel configuration that is in resonance with the transmitting circuit (Table 2).

TABLE 2

| RX Tank Circuit Characteristics | |
| --- | --- |
| Inductance | 25.69 µH |
| Capacitance | 400.2 nF |
| Coil Diameter | 5-cm |
| Coil Turns | 14 |

The catheter selected to be used in this work is 6.5 gauge and is 12 cm in length. The catheter is constructed in two parts—the inside stylet (or needle) and the outside sheath. Each part is connected to one side of the receiving LC circuit. These two parts are insulated from each other in order to only allow current to flow from the electrodes through the load.

The surface area of the electrodes is important to consider in order to predict and understand the ablation zone the catheter creates. The geometry of the inside stylet electrode is comprised of a hollow cylinder and a cone. Therefore, the surface area of this electrode is represented by equation 5. The surface area of the inside stylet electrode was calculated to be 67 mm².

$$SA_{inside\,stylet} = \pi d_{cyl} h_{cyl} + \frac{\pi d_{cyl}}{2} \sqrt{\left(\frac{d_{cone}}{2}\right)^2 + (h_{cone})^2} \quad (5)$$

The geometry of the outside sheath electrode is comprised of a hollow cylinder and its circular base that is represented as an annulus. Therefore, the surface area of this electrode is represented by equation 6. The surface area of the outside sheath electrode was calculated to be 79 mm².

$$SA_{outside\,sheath} = \pi d_{cyl} h_{cyl} + \pi\left(\left(\frac{d_1}{2}\right)^2 - \left(\frac{d_2}{2}\right)^2\right) \quad (6)$$

The catheter was constructed so that the surface area of the outside sheath electrode was 18% larger than the inside stylet electrode. This difference in surface areas directs the ablation zone toward the electrode with the smallest electrode surface area (17; 28). In this case, the electrode with the smaller surface area is the inside stylet electrode, therefore the ablation zone is closer to the tip of the catheter.

A thermistor is also inserted into the hollow catheter to measure the temperature at the tip of the catheter during ablation. The thermistor is connected to a small battery powered circuit that allows the catheter to be completely independent from any wired source.

Experimental Results

Figure 9:
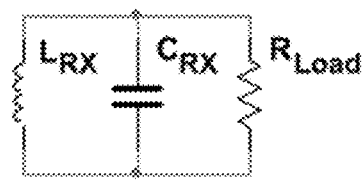
FIG. 9 shows a diagram of the Receiving (RX) Circuit during testing and ablation.

Four experiments were performed to evaluate the performance of the ablation system. The first and second tests directly focuses on the efficiency of the wireless power transfer. A resistor is connected to the RX coil and power is measured as the distance between the coils increase and as the input DC voltage changes. Then, the third test is to ablate ex vivo bovine tissue to evaluate the feasibility of this ablation system. For these experiments, the wireless catheter was connected in parallel to a load, either a resistor or animal tissue. This setup is represented by the circuit diagram found in FIG. 9.

Coil Distance and Power Efficiency with Resistive Load

The power of the ablation system was measured at the transmitting and receiving side to determine the efficiency of the wireless power transfer while the distance between the coils increased. In this experiment, a purely resistive load was added in parallel with the receiving tank circuit. The resistor was measured to be 103.1Ω☐ During this experiment the power received and its corresponding power efficiency at each coil distance will be observed. The distance between the coils is negatively proportional to the catheter insertion depth; as the catheter depth increases, the distance between the coils decrease.

Figure 10A:
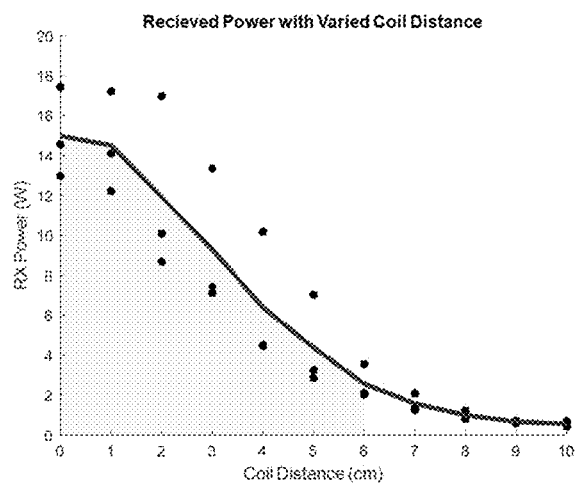
FIG. 10A-B shows received power (A) and efficiency (B) as coil distance increases.
Figure 10B:
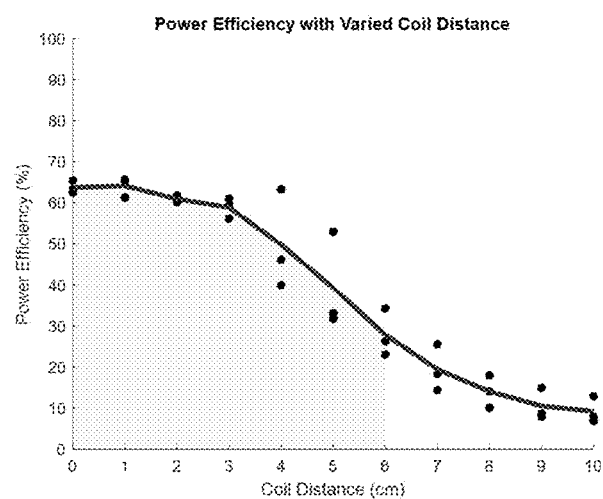

These tests were performed at a DC input voltage of 24 VDC, where the maximum transmitting power is possible. Three trials were conducted at each distance to determine the received power and efficiency. The mean of the received power and efficiency for the trials is shown FIG. 10. The largest received power and efficiency was achieved when the coils are at a contact distance. A maximum of 15 W±2 W was recorded at the load when the coils were at contact distance. As the coil distance increased, the received power and efficiency decreased. The minimum desired RX power is 3 W, powers less than this take extremely long to ablate with the presented catheter. Thus, a 6 cm coil distance is indicated as the maximum working distance.

Received Power and Varying DC Input Voltage with Resistive Load

When the presented ablation system is in use the only variables able to be manipulated are the catheter insertion depth and the DC input voltage. This experiment aims to determine the received power and the corresponding power efficiency as the DC input voltage varies. The operational voltage for the DC input ranges from 12 VDC to 24 VDC. In this experiment the power and efficiency were measured at increments of 1 VDC.

Figure 11A:
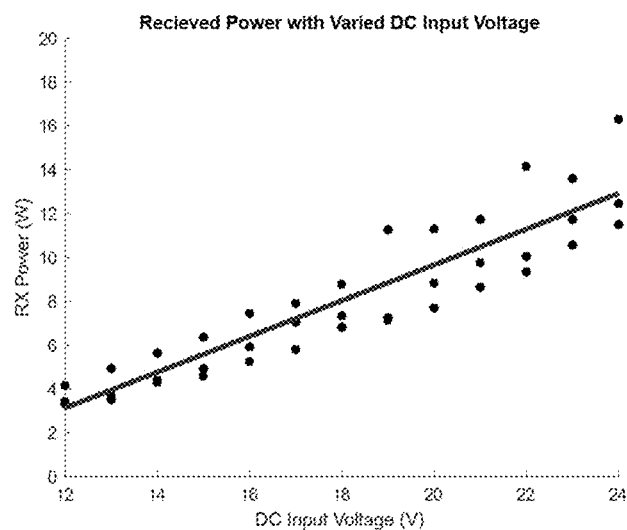
FIG. 11A-B shows received power (A) and efficiency (B) as DC input voltage increases.
Figure 11B:
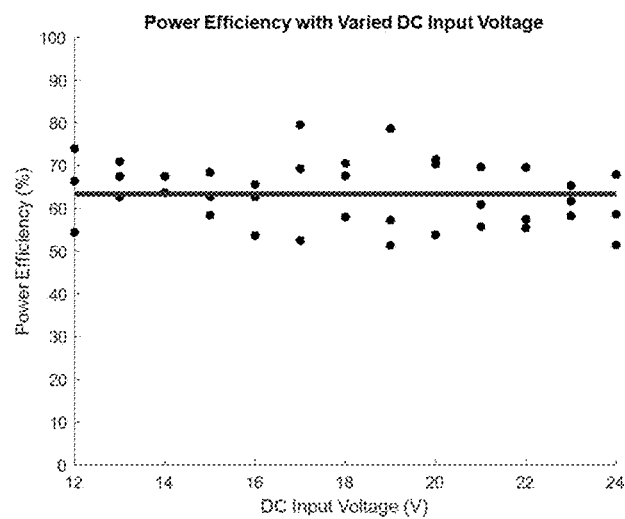

Since the coils remained at contact distance during these tests, the mutual inductance of the two tank circuits also stayed the same. Therefore, the efficiency was nearly the same for each regardless of the DC input voltage. The average efficiency recorded for all tests was 63.27% and the power received increased linearly as the DC input voltage increased (FIG. 11).

Ex Vivo Bovine Tissue Experiment

In this experiment, ex vivo bovine tissue was obtained to observe how the presented ablation system ablated tissue. Two tests were conducted—one with maximum ablation power and one with minimum ablation power. The temperature was recorded with the thermistor circuit on the wireless catheter. This tissue had an initial impedance of about 175Ω for all tests.

Maximum Power

Figure 13A:
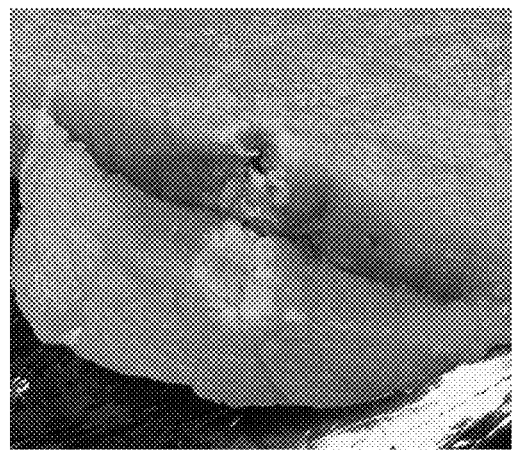
FIG. 13A-B shows results of maximum power test. (A) cross section of ablation zone, (B) ablation temperatures over time.
Figure 13B:
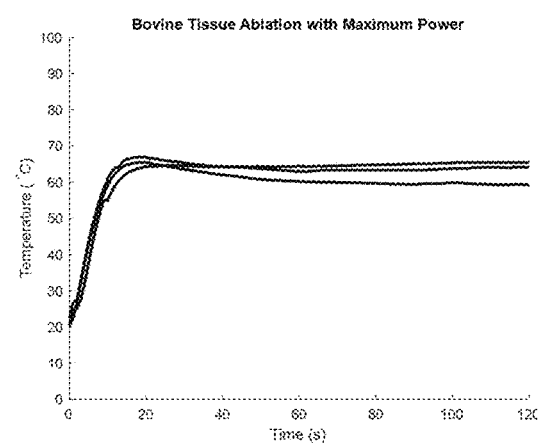

The first test was ablation at 24 VDC with the coils at contact distance. 3 trials were conducted for 2 minutes and the temperatures during ablations were plotted over time (FIG. 13b). From this data, a consistent temperature rise and decay was observed for each trial. The ablation zones were also nearly the same with a width of 9 mm and a length of 18 mm (FIG. 13a).

Minimum Power

Figure 14A:
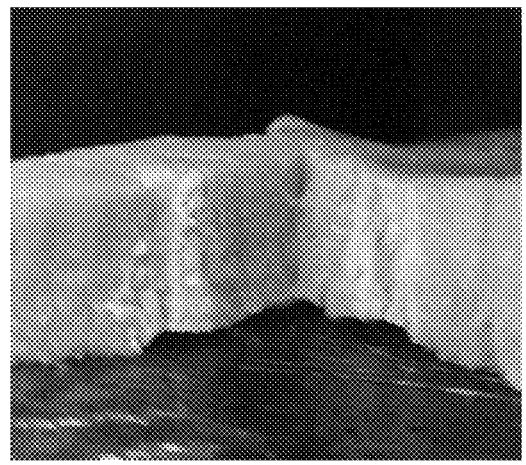
FIG. 14A-B shows results from the minimum power test. (A) cross section of ablation zone, (B) ablation temperatures over time.
Figure 14B:
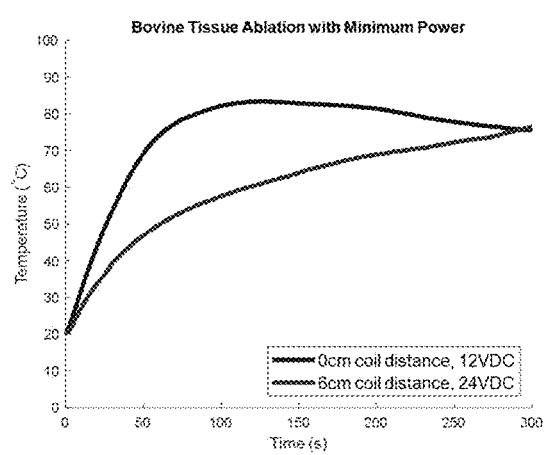

The next test was ablating the tissue at its minimum powers. This is achieved with an input voltage of 12 VDC at 0 cm coil distance and an input voltage of 24 VDC at 6 cm coil distance. The tissue was ablated for 5 minutes in each case and their temperatures during ablation were plotted over time (FIG. 14b). From the temperature data, the 12 VDC ablation had a faster rise in temperature because the power was slightly higher. The ablation at 6 cm distance had a lower power because the temperature rise was slower. However, the ablation zones for both tests were nearly the same with a width of 12 mm and a length of 21 mm.

CONCLUSION

A bipolar radiofrequency ablation system was developed to investigate the possibility of ablating tissue wirelessly. The system is comprised of the ablation generator and wireless catheter. The generator is comprised of an oscillating circuit that creates a medium power magnetic field. The catheter has a receiver coil that is induced with a voltage when placed in that magnetic field. The catheter has 2 electrodes that allow alternating current to flow through tissue.

To test the performance of this ablation system, tests were conducted to observe its received power, temperature, and ablation size. The maximum received power was 15 W±2 W where an average maximum efficiency of 63.27% was recorded. The ablation power and temperature was tested using ex vivo bovine tissue. The system was able to ablate up to a 2 cm ablation zone. With these results, the concept of using inductive power transfer to perform radiofrequency ablation wirelessly was proven.

REFERENCE LIST 1

[1] C. L. Brace, "Radiofrequency and microwave ablation of the liver, lung, kidney, and bone: what are the differences?," *Current problems in diagnostic radiology*, vol. 38, no. 3, pp. 135-143, 2009.

[2] D. E. Haines, "The biophysics of radiofrequency catheter ablation in the heart: the importance of temperature monitoring," *Pacing and Clinical Electrophysiology*, vol. 16, no. 3, pp. 586-591, 1993.

[3] S. N. Goldberg, G. S. Gazelle, L. Solbiati, W. J. Rittman, and P. R. Mueller, "Radiofrequency tissue ablation: increased lesion diameter with a perfusion electrode," *Academic radiology*, vol. 3, no. 8, pp. 636-644, 1996.

[4] S. Labonte, "Numerical model for radio-frequency ablation of the endocardium and its experimental validation," *IEEE Transactions on Biomedical Engineering*, vol. 41, no. 2, pp. 108-115, 1994.

[5] E. J. Berjano, "Theoretical modeling for radiofrequency ablation: state-of-the-art and challenges for the future," *Biomedical engineering online*, vol. 5, no. 1, p. 24, 2006.

[6] S. N. Goldberg, M. C. Stein, G. S. Gazelle, R. G. Sheiman, J. B. Kruskal, and M. E. Clouse, "Percutaneous radiofrequency tissue ablation: optimization of pulsed-radiofrequency technique to increase coagulation necrosis," *Journal of vascular and interventional radiology*, vol. 10, no. 7, pp. 907-916, 1999.

[7] I. S. Jesus, J. Machado, J. B. Cunha, and M. F. Silva, "Fractional order electrical impedance of fruits and vegetables," in *Proceedings of the 25th IASTED international conference on Modeling, indentification, and control*, 2006, pp. 489-494: ACTA Press.

[8] D. Haemmerich, T. Staelin, S. Tungjitkusolmun, F. T. Lee, D. M. Mahvi, and J. G. Webster, "Hepatic bipolar radio-frequency ablation between separated multiprong electrodes," *IEEE Transactions on Biomedical Engineering*, vol. 48, no. 10, pp. 1145-1152, 2001.

[9] D. Haemmerich, "Mathematical modeling of impedance controlled radiofrequency tumor ablation and ex-vivo validation," in *Engineering in Medicine and Biology Society (EMBC), 2010 Annual International Conference of the IEEE*, 2010, pp. 1605-1608: IEEE.

[10] J. I. Agbinya, *Wireless power transfer*. River Publishers, 2015.

[11] T. Morimoto et al., "A Study of the Electrical Bio-impedance of Tumors," *Journal of Investigative Surgery*, vol. 6, no. 1, pp. 25-32, 1993 Jan. 1.

REFERENCE LIST 2

1. Blessing E, Esler M D, Francis D P, Schmieder REJJCI. 2013. Cardiac ablation and renal denervation systems have distinct purposes and different technical requirements. 6:314
2. Patel N, Gross A, Brown L, Gekht GJPM. 2012. A randomized, placebo-controlled study to assess the efficacy of lateral branch neurotomy for chronic sacroiliac joint pain. 13:383-98
3. Joo Y-C, Park J-Y, Kim K-HJJoa. 2013. Comparison of alcohol ablation with repeated thermal radiofrequency ablation in medial branch neurotomy for the treatment of recurrent thoracolumbar facet joint pain. 27:390-5
4. Livraghi T, Goldberg S N, Lazzaroni S, Meloni F, Solbiati L, Gazelle GSJR. 1999. Small hepatocellular carcinoma: treatment with radio-frequency ablation versus ethanol injection. 210:655-61
5. Pearson A S, Izzo F, Fleming R D, Ellis L M, Delrio P, et al. 1999. Intraoperative radiofrequency ablation or cryoablation for hepatic malignancies. 178:592-8
6. Souchon R, Rouvière O, Gelet A, Detti V, Srinivasan S, et al. 2003. Visualisation of HIFU lesions using elastography of the human prostate in vivo: preliminary results. 29:1007-15
7. Vogel A, Venugopalan VJCr. 2003. Mechanisms of pulsed laser ablation of biological tissues. 103:577-644
8. Brace C L. 2009. Radiofrequency and microwave ablation of the liver, lung, kidney, and bone: what are the differences? *Current problems in diagnostic radiology* 38:135-43
9. Curley SAJAoSO. 2003. Radiofrequency ablation of malignant liver tumors. 10:338-47
10. Mirza A N, Fornage B D, Sneige N, Kuerer H M, Newman L A, et al. 2001. Radiofrequency ablation of solid tumors. 7:95-102
11. Goldberg S N, Gazelle G S, Solbiati L, Rittman W J, Mueller P R. 1996. Radiofrequency tissue ablation: increased lesion diameter with a perfusion electrode. *Academic radiology* 3:636-44
12. Haines D E. 1993. The biophysics of radiofrequency catheter ablation in the heart: the importance of temperature monitoring. *Pacing and Clinical Electrophysiology* 16:586-91
13. Haemmerich D. 2010. Biophysics of radiofrequency ablation. *Critical Reviews™ in Biomedical Engineering* 38
14. Morimoto T, Kimura S, Konishi Y, Komaki K, Uyama T, et al. 1993. A Study of the Electrical Bio-impedance of Tumors. *Journal of Investigative Surgery* 6:25-32
15. Haemmerich D. Mathematical modeling of impedance controlled radiofrequency tumor ablation and ex-vivo validation. *Proc. Engineering in Medicine and Biology Society (EMBC), 2010 Annual International Conference of the IEEE*, 2010:1605-8: IEEE
16. Haemmerich D, Staelin T, Tungjitkusolmun S, Lee F T, Mahvi D M, Webster J G. 2001. Hepatic bipolar radio-frequency ablation between separated multiprong electrodes. *IEEE Transactions on Biomedical Engineering* 48:1145-52
17. Nakada S Y, Jerde T J, Warner T F, Wright A S, Haemmerich D, et al. 2003. Bipolar radiofrequency ablation of the kidney: comparison with monopolar radiofrequency ablation. 17:927-33
18. Decadt B, Siriwardena AKJTlo. 2004. Radiofrequency ablation of liver tumours: systematic review. 5:550-60
19. McGahan J P, Dodd III GDJAJoR. 2001. Radiofrequency ablation of the liver: current status. 176:3-16
20. Boeti M P S, Grigorie Rz, Popescu I. 2013. Laparoscopic radiofrequency ablation of liver tumors. In *Hepatic Surgery*: IntechOpen. Number of
21. Machi J, Uchida S, Sumida K, Limm W M, Hundahl S A, et al. 2001. Ultrasound-guided radiofrequency thermal ablation of liver tumors: percutaneous, laparoscopic, and open surgical approaches. 5:477-89
22. Agbinya J I. 2015. *Wireless power transfer*. River Publishers
23. Kim K Y. 2012. *Wireless power transfer-principles and engineering explorations*.

24. Stielau O H, Covic G A. Design of loosely coupled inductive power transfer systems. *Proc. PowerCon 2000. 2000 International Conference on Power System Technology. Proceedings (Cat. No. 00EX409)*, 2000, 1:85-90: IEEE
25. William B T. 1995. *Advanced Electromagnetism: Foundations: Theory And Applications*. World Scientific
26. Costanzo A, Dionigi M, Mastri F, Mongiardo M. Rigorous modeling of mid-range wireless power transfer systems based on Royer oscillators. *Proc. 2013 IEEE Wireless Power Transfer (WPT)*, 2013:69-72: IEEE
27. Mastri F, Costanzo A, Dionigi M, Mongiardo M. Harmonic balance design of wireless resonant-type power transfer links. *Proc. 2012 IEEE MTT-S International Microwave Workshop Series on Innovative Wireless Power Transmission: Technologies, Systems, and Applications*, 2012:245-8: IEEE
28. Kovoor P, Daly M, Pouliopoulos J, Dewsnap M B, Eipper V, et al. 2005. Effect of Inter-electrode Distance on Bipolar Intramural Radiofrequency Ablation. 28:514-20

Publications cited herein are hereby specifically incorporated by reference in their entireties and at least for the material for which they are cited.

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

What is claimed is:

1. A wireless tissue ablation device comprising:
   an alternating magnetic field generator;
   an ablation probe comprising an ablation tip and a first electrical lead;
   a catheter comprising an opening at a tissue insertion end and a lumen extending along a length of the catheter to the catheter opening, wherein the catheter comprises an electrically conductive material forming a second electrical lead; and
   a magnetic field receiving coil attached to the catheter, wherein the magnetic field receiving coil is electrically coupled to the second electrical lead;
   wherein at least a portion of the ablation probe is positionable within the lumen of the catheter such that a conductive circuit is completed when the first electrical lead of the ablation probe contacts the second electrical lead of the catheter during ablation, and wherein the ablation tip protrudes through the opening of the catheter.

2. The device of claim 1, wherein the alternating magnetic field generator comprises a magnetic field transmitting coil.

3. The device of claim 1, wherein the alternating magnetic field generator is powered by a battery.

4. The device of claim 1, wherein the alternating magnetic field generator is comprised within a portable housing, wherein the total weight of the portable housing comprising the alternating magnetic field generator is ten pounds or less.

5. The device of claim 4, wherein the portable housing comprises an elongated bottom surface configured to contact the subject.

6. The device of claim 4, wherein the portable housing further comprises a top surface and an access opening extending from the top surface to an elongated bottom surface, wherein the access opening provides access to the subject upon positioning the portable housing on the subject.

7. The device of claim 6, wherein the access opening of the portable housing has a width of five inches or less.

8. The device of claim 1, wherein the portion of the ablation probe positionable within the lumen of the catheter comprises a probe outer surface electrical insulator.

9. The device of claim 1, wherein the magnetic field transmitting coil and the magnetic field receiving coil are configured to resonate at a frequency from about 200 kHz to about 240 kHz.

10. The device of claim 1, wherein the magnetic field receiving coil is positioned on an electrically insulated stop barrier attached to the catheter.

11. A method of ablating a target tissue in a subject, the method comprising:
    positioning in the subject a catheter comprising an opening at a tissue insertion end and a lumen, wherein the catheter comprises an electrically conductive material forming a second electrical lead;
    contacting the target tissue with an ablation tip of an ablation probe and having a first electrical lead, wherein at least a portion of the ablation probe is positioned within the lumen of the catheter, and wherein the ablation tip protrudes through the opening of the catheter;
    generating a magnetic field from an alternating magnetic field generator to wirelessly induce a current in a magnetic field receiving coil, wherein the magnetic field receiving coil is attached to the catheter and electrically coupled to the second electrical lead such that a conductive circuit is completed when the first electrical lead of the ablation probe contacts the second electrical lead of the catheter during ablation; and
    electrically energizing the ablation tip, thereby ablating the target tissue.

12. The method of claim 11, wherein the alternating magnetic field generator comprises a magnetic field transmitting coil.

13. The method of claim 11, wherein the alternating magnetic field generator is comprised within a portable housing.

14. The method of claim 13, further comprising positioning the portable housing on the subject adjacent to a catheter insertion point.

15. The method of claim 11, wherein the magnetic field receiving coil is coupled to the catheter such that positioning the catheter in the subject also positions the magnetic field receiving coil within 12 cm or less of the alternating magnetic field generator.

16. The method of claim 15, wherein positioning the catheter in the subject also positions the magnetic field receiving coil within 1 cm or less of the alternating magnetic field generator.

17. The method of claim 12, wherein the magnetic field transmitting coil and the magnetic field receiving coil each oscillate within a range of frequencies from 200 kHz to 240 kHz.

18. The method of claim 17, wherein the oscillation frequency of the magnetic field receiving coil is within 5 kHz of the oscillation frequency of the magnetic field transmitting coil, thereby resonance coupling the magnetic field receiving coil and the magnetic field transmitting coil at a resonance frequency.

19. The method of claim 18, further comprising coupling a resonance converter to the magnetic receiving coil, wherein the resonance converter adjusts the current to maintain resonance coupling between the magnetic field receiving coil and the magnetic field transmitting coil.

20. The method of claim 11, wherein the alternating magnetic field generator has a power output of at least 25 W, and the ablation probe has a power output of at least 15 W.

* * * * *